United States Patent [19]

Madou et al.

[11] Patent Number: 4,948,680
[45] Date of Patent: Aug. 14, 1990

[54] SOLID COMPOSITIONS FOR FUEL CELL ELECTROLYTES

[75] Inventors: Marc J. Madou, Palo Alto; Takaaki Otagawa, Fremont; Arden Sher, Foster City, all of Calif.

[73] Assignee: SRI International, Menlo Park, Calif.

[21] Appl. No.: 196,498

[22] Filed: May 20, 1988

Related U.S. Application Data

[63] Continuation-in-part of Ser. No. 935,289, Nov. 26, 1989, Pat. No. 4,851,303.

[51] Int. Cl.$^5$ ............................................. H01M 8/10
[52] U.S. Cl. ......................................... 429/13; 429/33; 429/40; 252/62.2; 501/151; 501/152
[58] Field of Search .................. 429/30, 33, 40, 13; 501/151, 152; 252/62.2

[56] References Cited

U.S. PATENT DOCUMENTS

| | | | |
|---|---|---|---|
| 3,698,955 | 10/1972 | Lilly et al. | 429/33 X |
| 4,052,532 | 10/1977 | Tannenberger et al. | 429/33 |
| 4,598,467 | 7/1986 | Isenberg et al. | 429/33 X |

FOREIGN PATENT DOCUMENTS 1070937 6/1967 United Kingdom ................. 429/33

OTHER PUBLICATIONS

Sarni et al., *Chemical Abstracts*, vol. 98, No. 207773, 1983.
Argile et al., *Chemical Abstracts*, vol. 90, No. 59350, 1979.

*Primary Examiner*—Stephen J. Kalafut
*Attorney, Agent, or Firm*—Phillips, Moore Lempio & Finley

[57] ABSTRACT

The present invention relates to solid materials for use as solid electrolytes for a fuel cell. Specifically, the invention relates to a solid $O^{2-}$ conducting material for use as an electrolyte for a fuel cell, comprising:

a monocrystal or polycrystal structure of the formula: $A_{1-x}B_xZ$, wherein

A is independently selected from lanthanum, cerium, neodymium, praseodymium, scandium or mixtures thereof;

B is independently selected from strontium, calcium, barium or magnesium, and x is between about 0 and 0.9999, Z is selected from the group consisting of $F_{3-x}$ and $O_cF_d$ where F is fluorine, O is oxygen, x is between about 0 and 0.9999 and $2c+d=3-x$, wherein c is between 0.0001 and 1.5 and d is between 0.0001 and less than or equal to 3, with the proviso when A is lanthanum, Z is $F_{3-x}$ and x is 0, the solid material is only a monocrystal. In another aspect the present invention relates to a composite fuel cell of thin lanthanum strontium fluoride having a laminate (composite)-type structure. In another aspect, the solid electrolyte for a fuel cell is a monocrystal or polycrystal structure of $Pb_eSn_fF_g$, where Pb is lead and Sn is tin. The invention also includes the use of the solid electrolyte fuel cells disclosed to generate electricity.

32 Claims, 26 Drawing Sheets

*Table I. Fuel cell types*

| | Phosphoric Acid | Molten Carbonate | Alkaline | High-Temperature Solid Oxide | Solid Polymer |
|---|---|---|---|---|---|
| Electrolyte | Conc. $H_3PO_4$ | $K_2CO_3$-$Li_2CO_3$ | KOH solution | $ZrO_2$-$Y_2O_3$ or $ZrO_2$-CaO | Sulfonated fluoro-carbon acidic ion exchange membrane |
| Electrolyte support | Phenolic fiber(SiC) | $LiAlO_2$ | Asbestos | Electrolyte itself | Electrolyte itself |
| Electrode (catalyst) | Pt | Ni, NiO | Pt, Pt-Au alloy | NiO-$ZrO_3$- $La_{0.9}Sr_{0.1}MnO_3$ | Pt |
| Anode fuel | $H_2$(reformer product) | $H_2$-CO | $H_2$(high purity) | $H_2$-CO | $H_2$ |
| Cathode oxidant | Air | Air +$CO_2$ | $O_2$(high purity) | Air | $O_2$ |
| Temperature (°C) | 160-190 | 600-700 | 82-104 | 900-1100 | 82 |
| Pressure (atm) | <120 psia | <120 psia | 60 psia | Atm | 60 psia |

FIG._IA
Table I. Fuel cell types

| | Phosphoric Acid | Molten Carbonate | Alkaline | High-Temperature Solid Oxide | Solid Polymer |
|---|---|---|---|---|---|
| Electrolyte | Conc. $H_3PO_4$ | $K_2CO_3-Li_2CO_3$ | KOH solution | $ZrO_2-Y_2O_3$ or $ZrO_2-CaO$ | Sulfonated fluorocarbon acidic ion exchange membrane |
| Electrolyte support | Phenolic fiber (SiC) | $LiAlO_2$ | Asbestos | Electrolyte itself | Electrolyte itself |
| Electrode (catalyst) | Pt | Ni, NiO | Pt, Pt-Au alloy | $NiO-ZrO_3-La_{0.9}Sr_{0.1}MnO_3$ | Pt |
| Anode fuel | $H_2$ (reformer product) | $H_2-CO$ | $H_2$ (high purity) | $H_2-CO$ | $H_2$ |
| Cathode oxidant | Air | Air + $CO_2$ | $O_2$ (high purity) | Air | $O_2$ |
| Temperature (°C) | 160-190 | 600-700 | 82-104 | 900-1100 | 82 |
| Pressure (atm) | <120 psia | <120 psia | 60 psia | Atm | 60 psia |

| | | | | | |
|---|---|---|---|---|---|
| Cell voltage (V) | <0.8 | <0.85 | <0.97 | <0.90 | <0.95 |
| Impurity tolerance | <2000 ppm CO" <1 ppm H$_2$S" | No H$_2$S | High-purity feeds, no CO and CO$_2$ | Not yet defined | Strict moisture control |
| Development status | Nearest to commercialization | Next nearest to commercialization | Apollo and Columbia space flights | Third-generation technology | Gemini space flights |
| Anodic reaction | H$_2$ → 2H$^+$ + 2e$^-$ | H$_2$ + CO$_3^{-2}$ → H$_2$O(g) + CO$_2$ + 2e$^-$ | H$_2$ + 2OH$^-$ → 2H$_2$O(g) + 2e$^-$ | H$_2$ + O$^{-2}$ → H$_2$O(g) + 2e$^-$ or CO + O$^{-2}$ → CO$_2$ + 2e$^-$ | H$_2$ → 2H$^+$ + 2e$^-$ |
| Cathodic reaction | 2e$^-$ + ½O$_2$ + 2H$^+$ → H$_2$O(g) | CO$_2$ + ½O$_2$ + 2e$^-$ → CO$_3^{-2}$ | H$_2$O + ½O$_2$ + 2e$^-$ → 2OH$^-$ | ½O$_2$ + 2e$^-$ → O$^{2-}$ | 2H$^+$ + ½O$_2$ + 2e$^-$ → H$_2$O |
| Overall reaction | H$_2$ + ½O$_2$ → H$_2$O(g) | H$_2$ + ½O$_2$ → H$_2$O(g) | H$_2$ + ½O$_2$ → H$_2$O(l) | H$_2$ + ½O$_2$ → H$_2$O(g) H$_2$ + ½O$_2$ → CO$_2$ or CO + ½O$_2$ → CO$_2$ | H$_2$ + ½O$_2$ → H$_2$O(l) |

FIG._1B

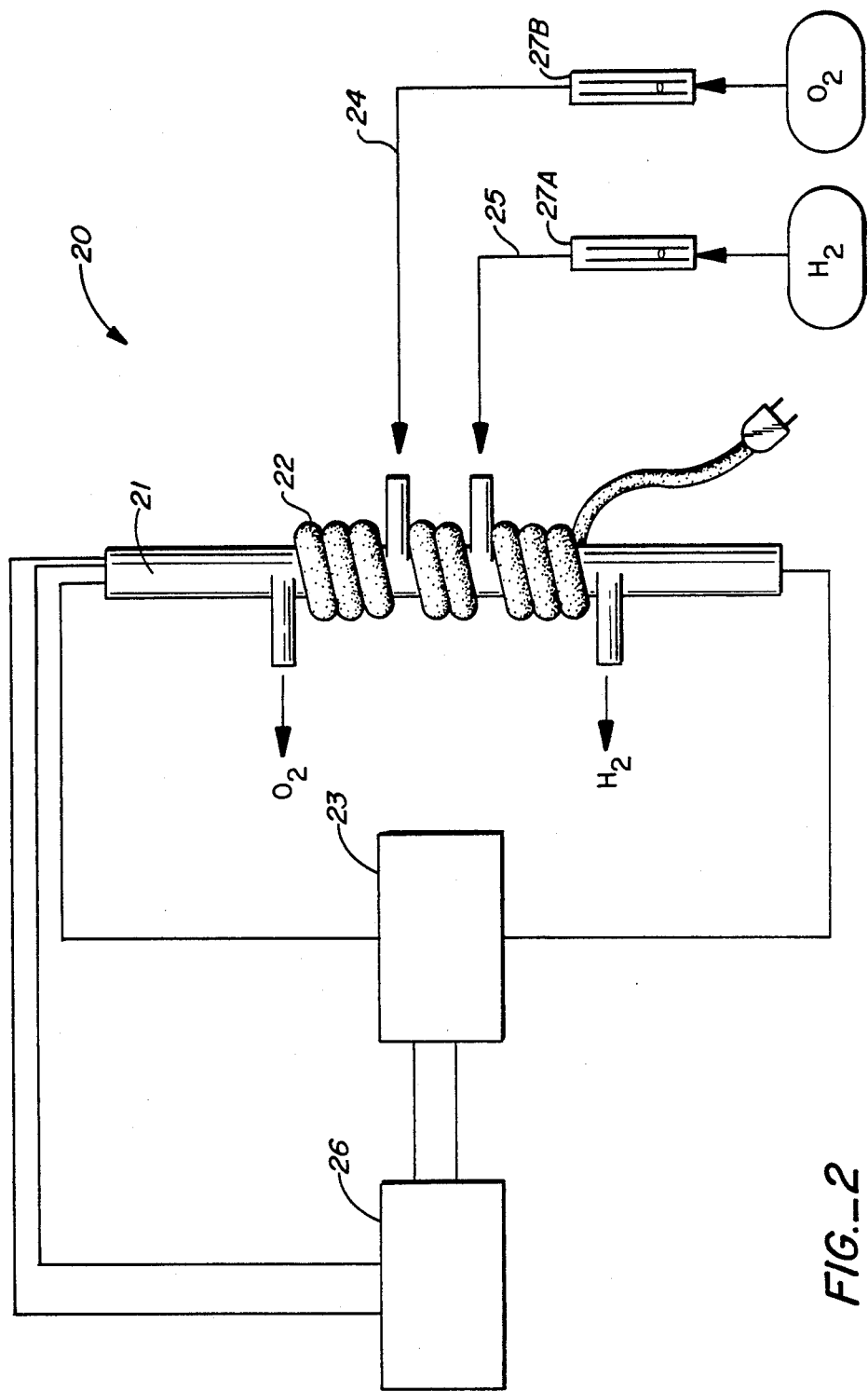
FIG._2

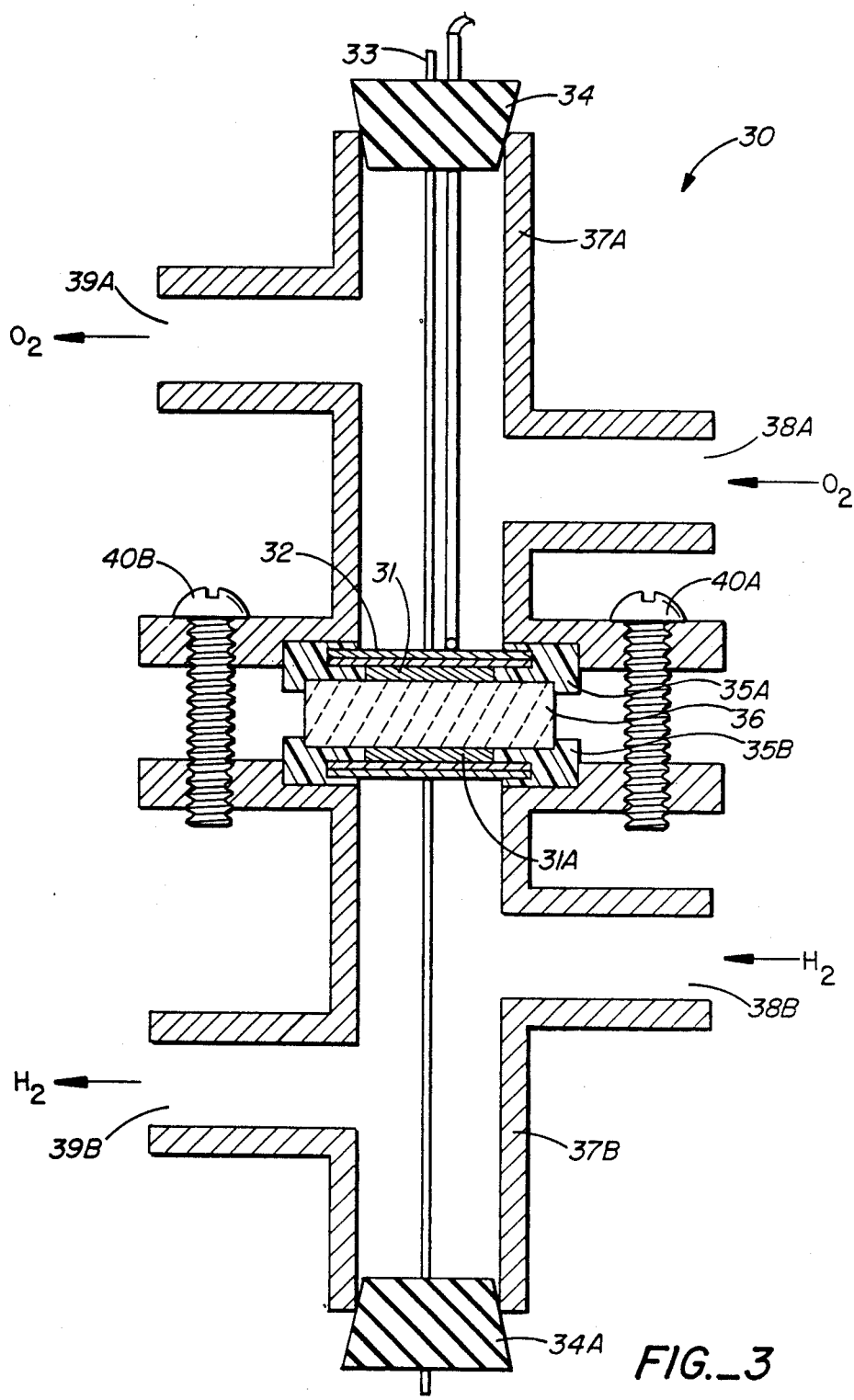
FIG._3

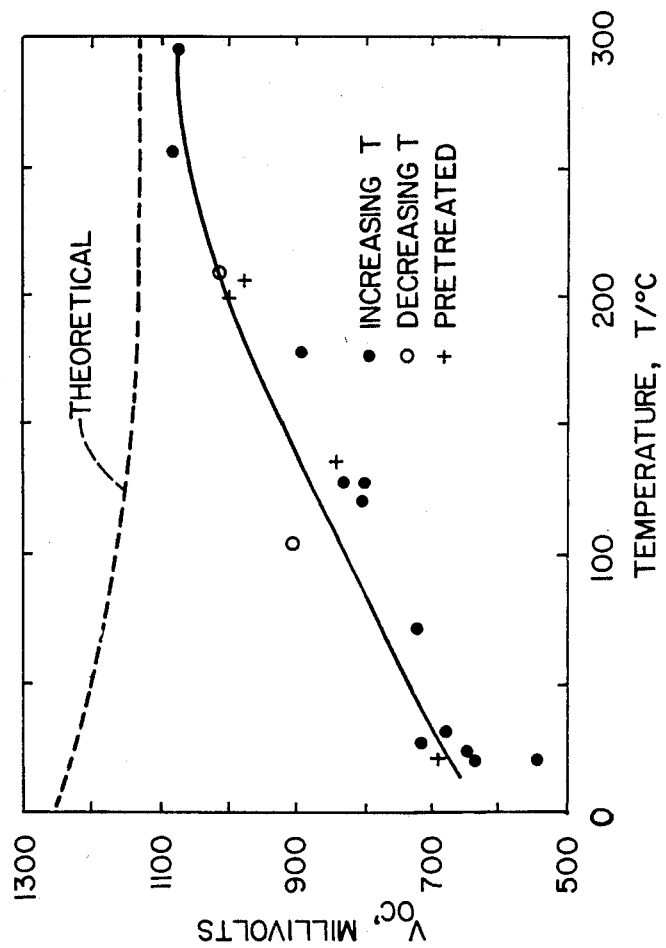
FIG._4

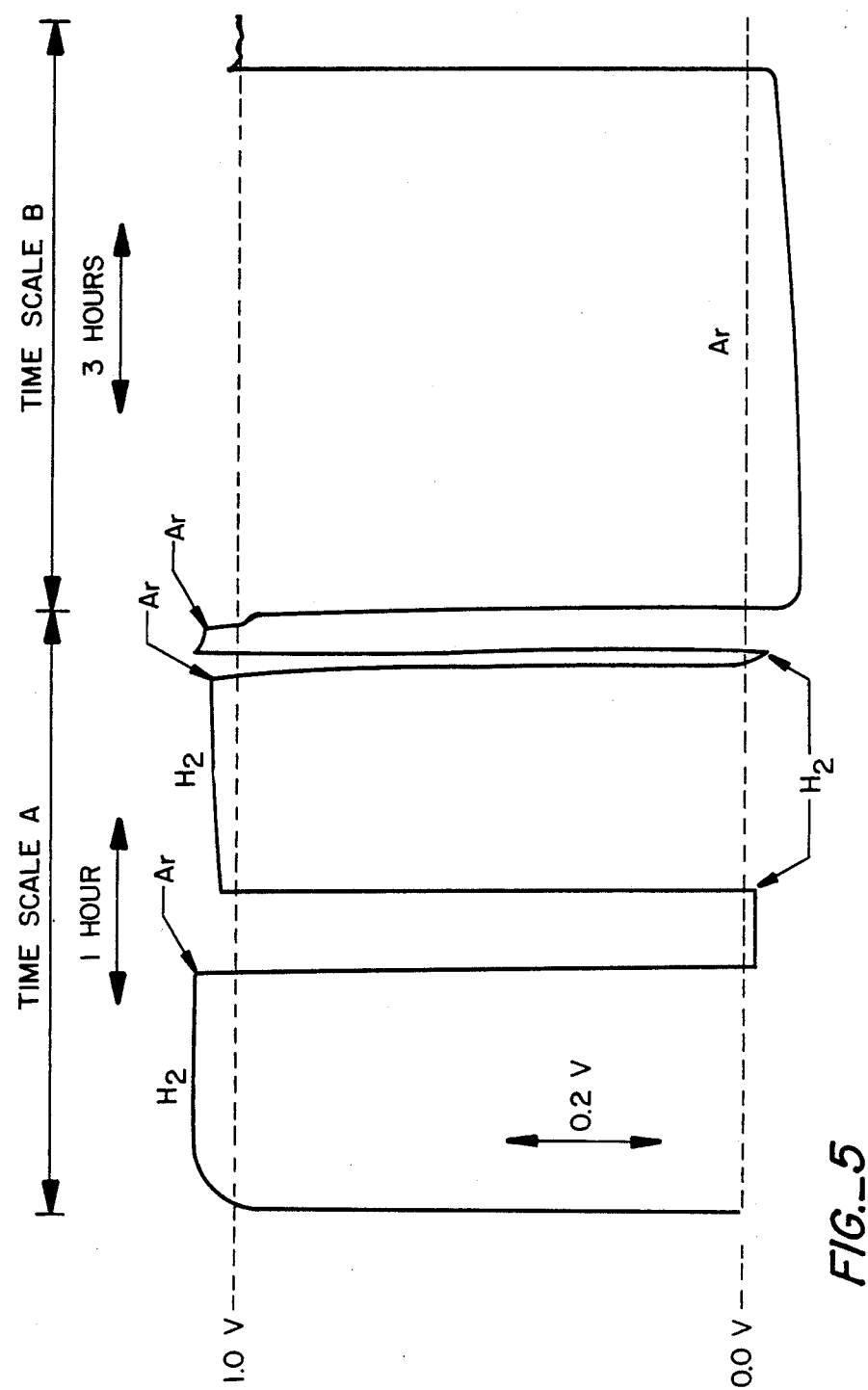
FIG._5

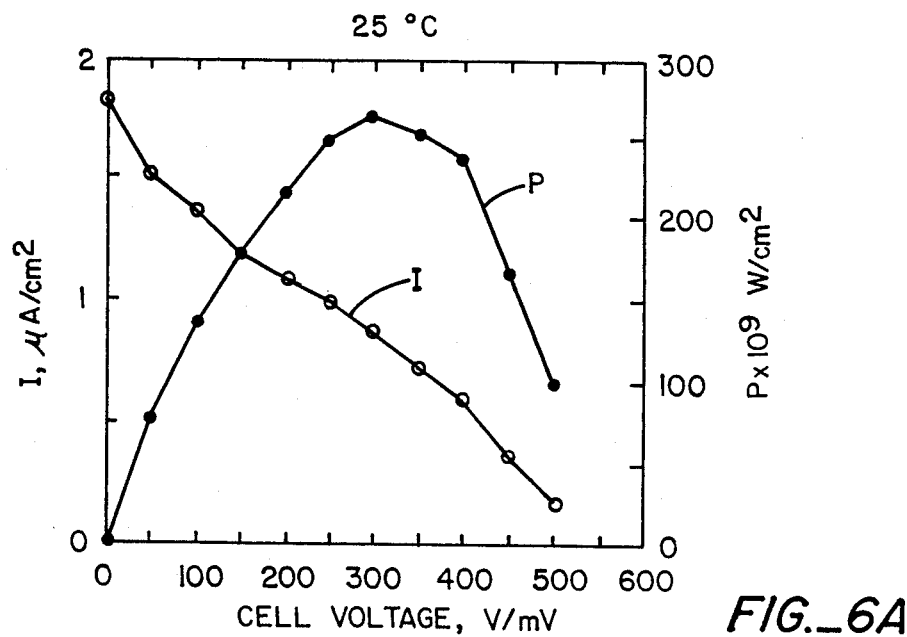
FIG._6A
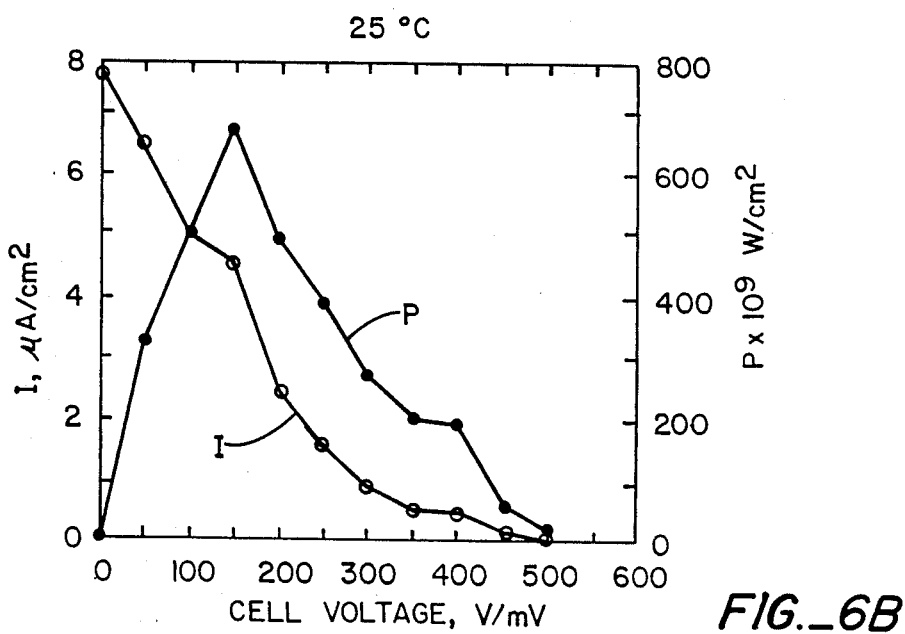
FIG._6B

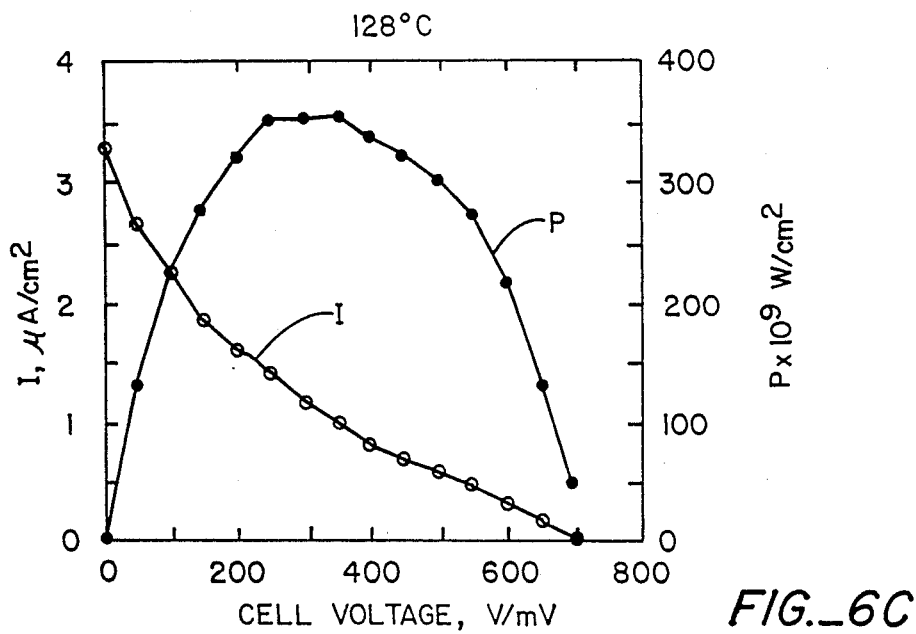
FIG._6C
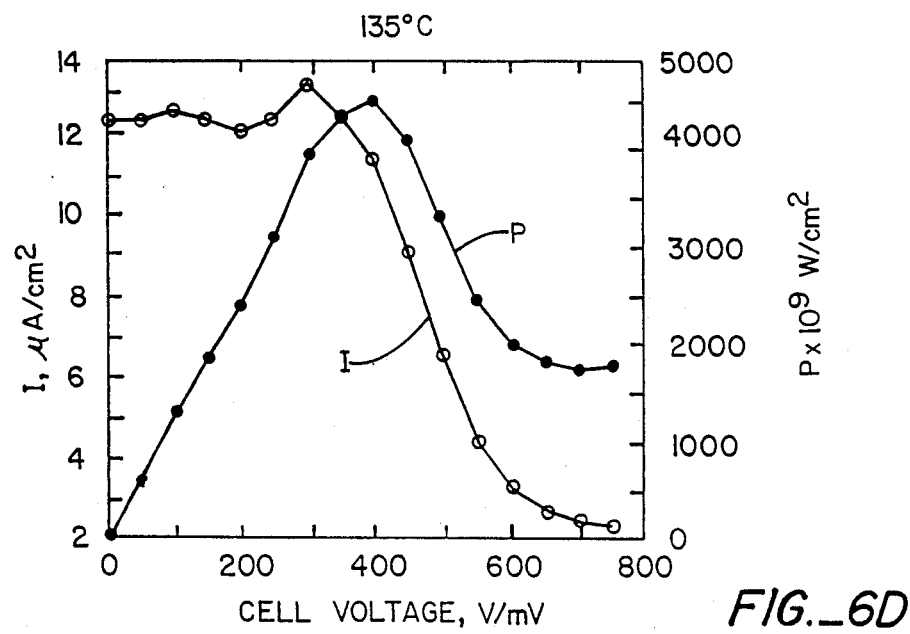
FIG._6D

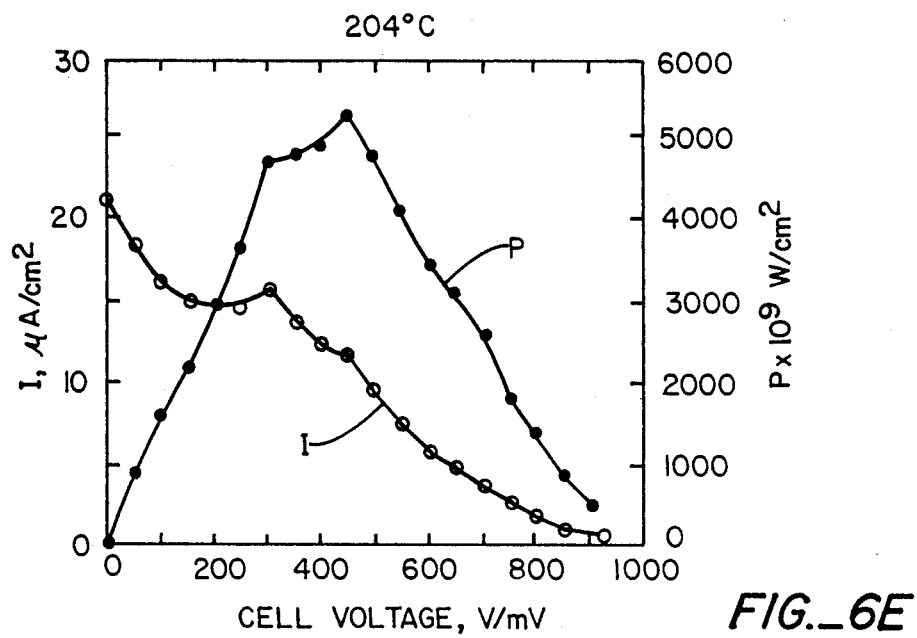
FIG._6E
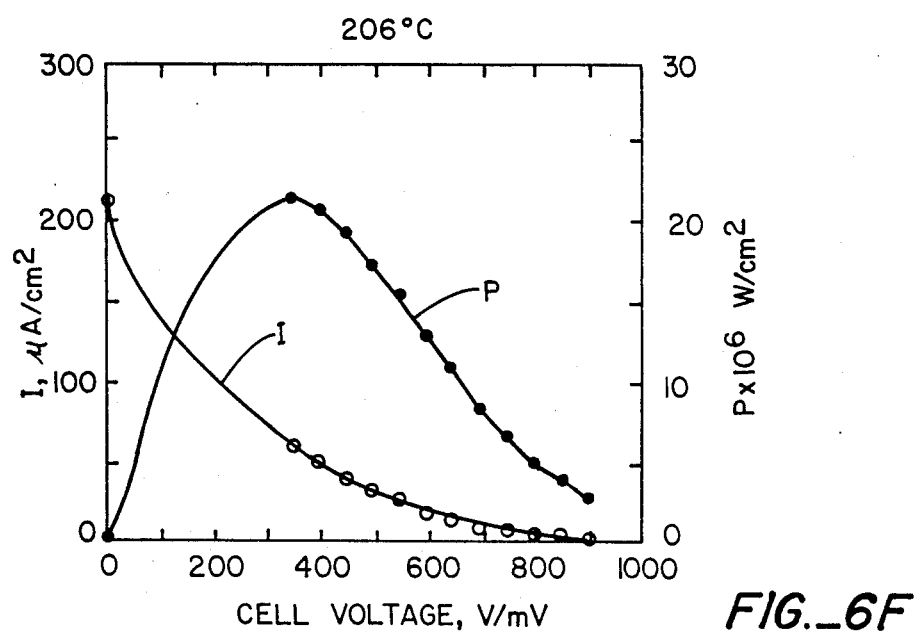
FIG._6F

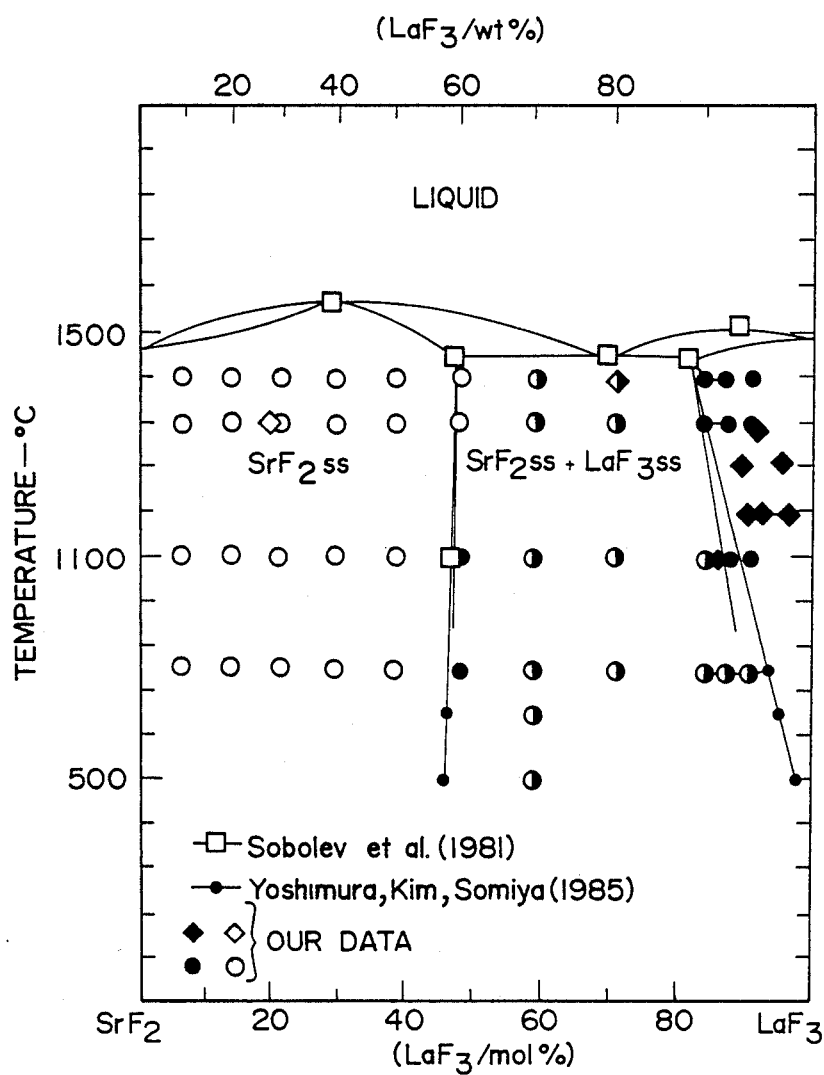
FIG._7

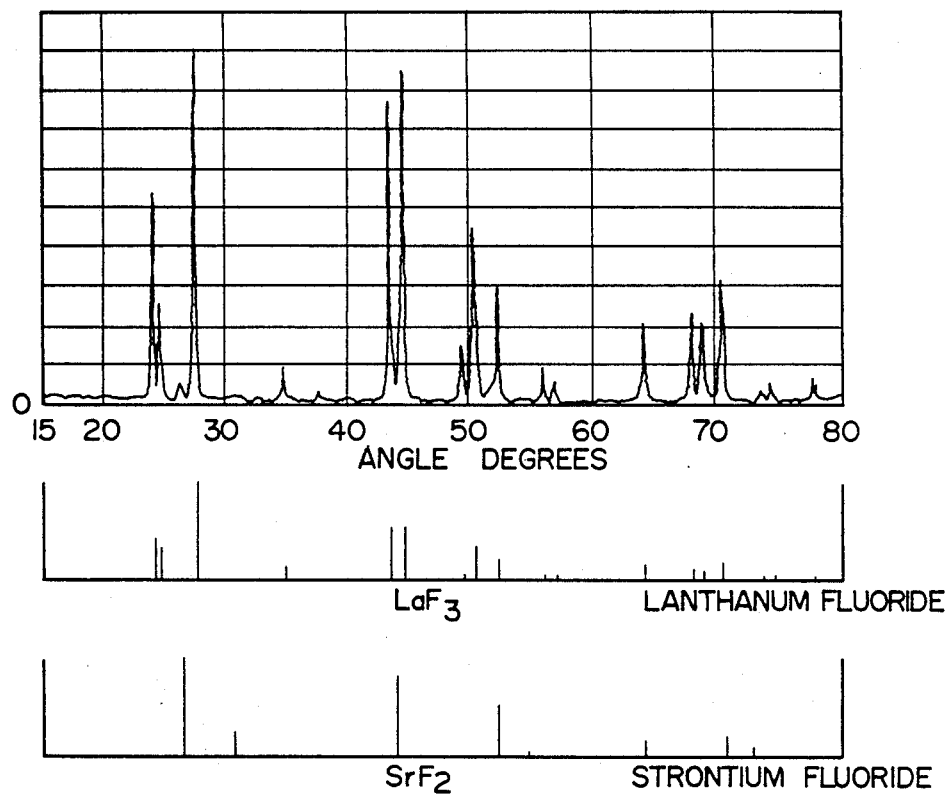
FIG._8

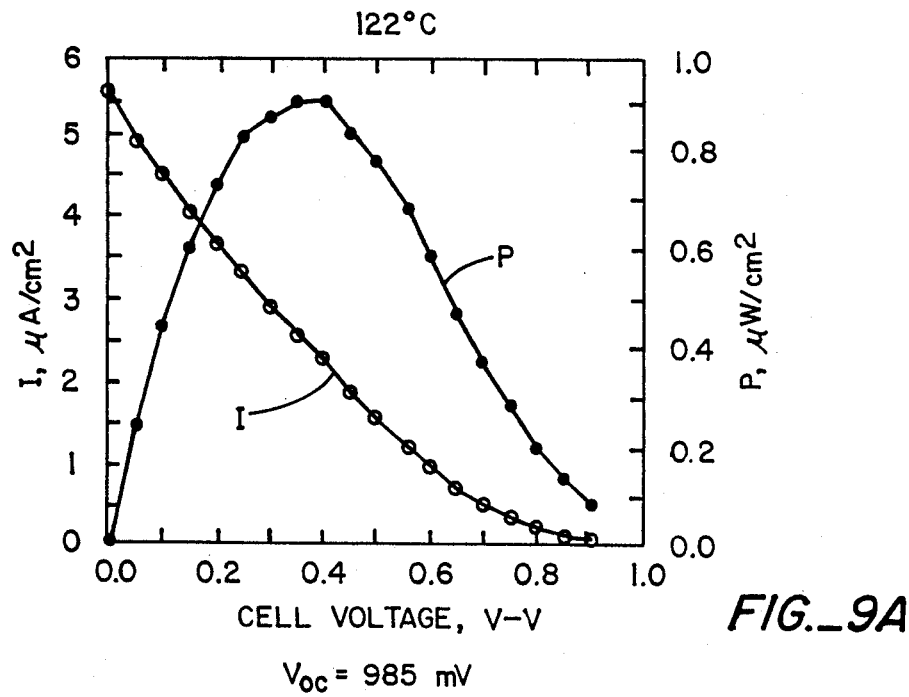
FIG._9A
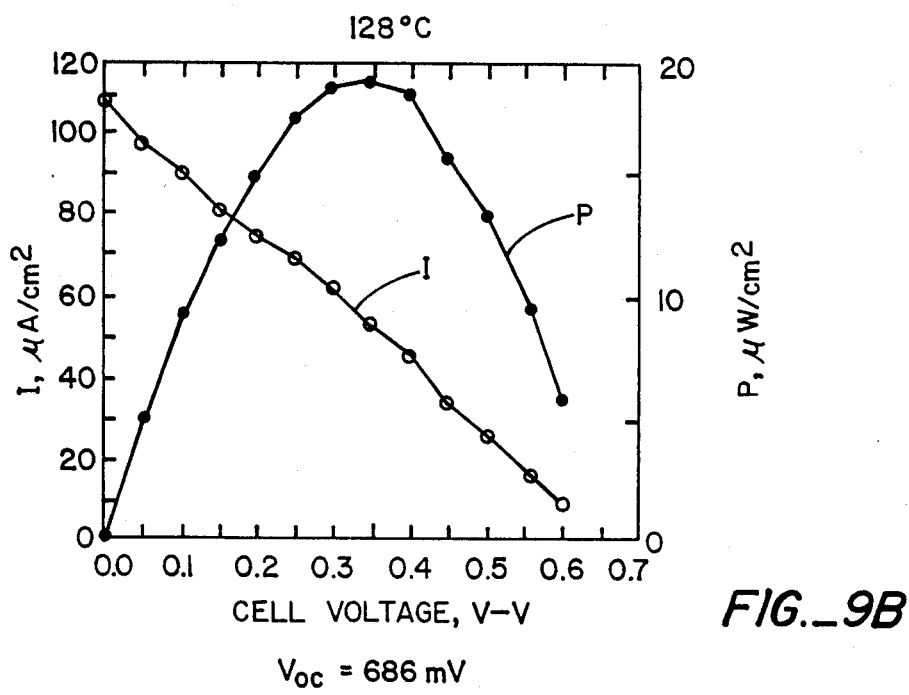
FIG._9B

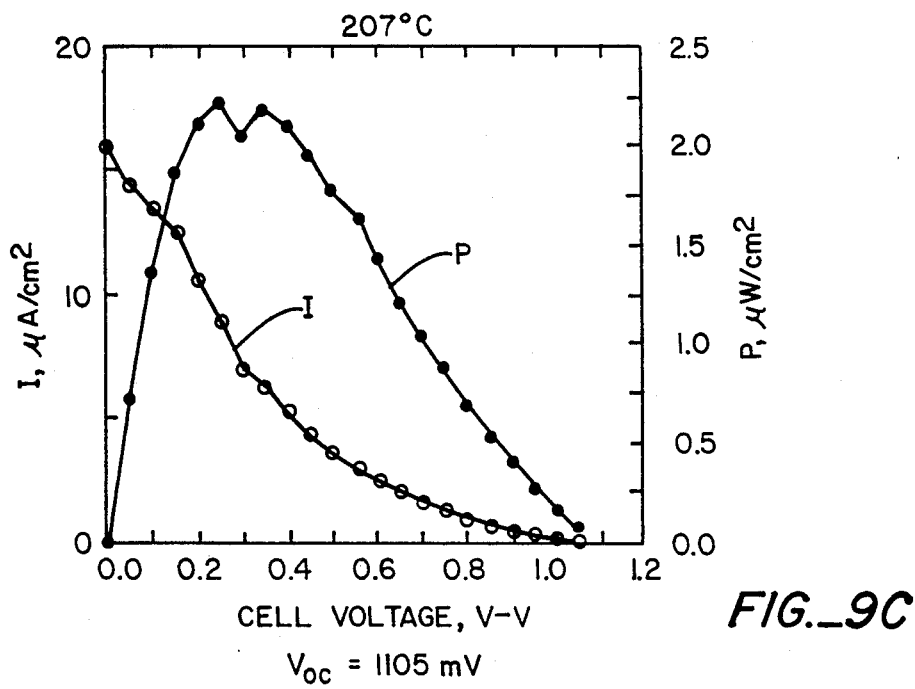
*FIG._9C*
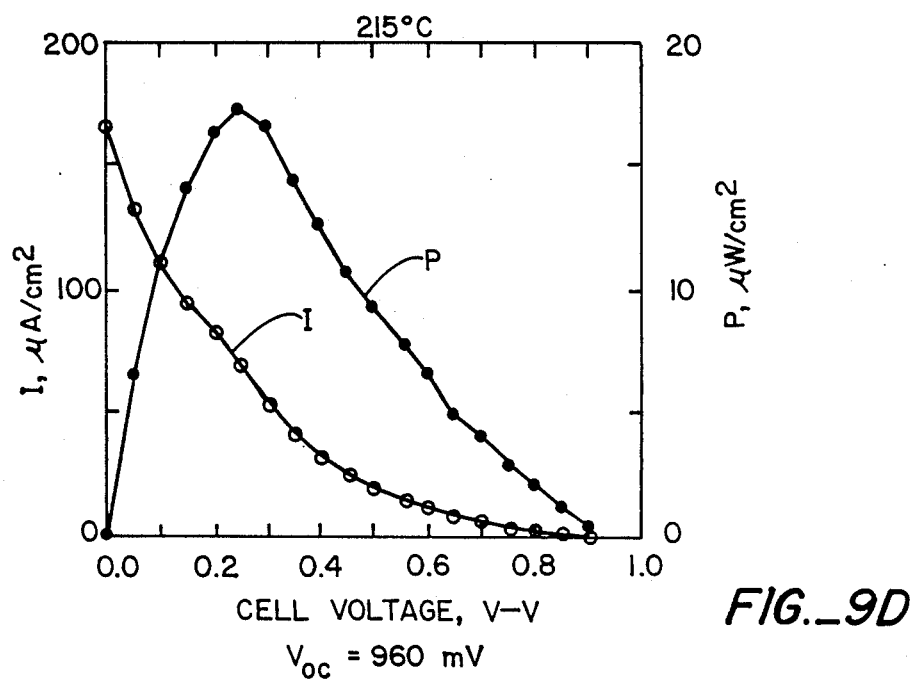
*FIG._9D*

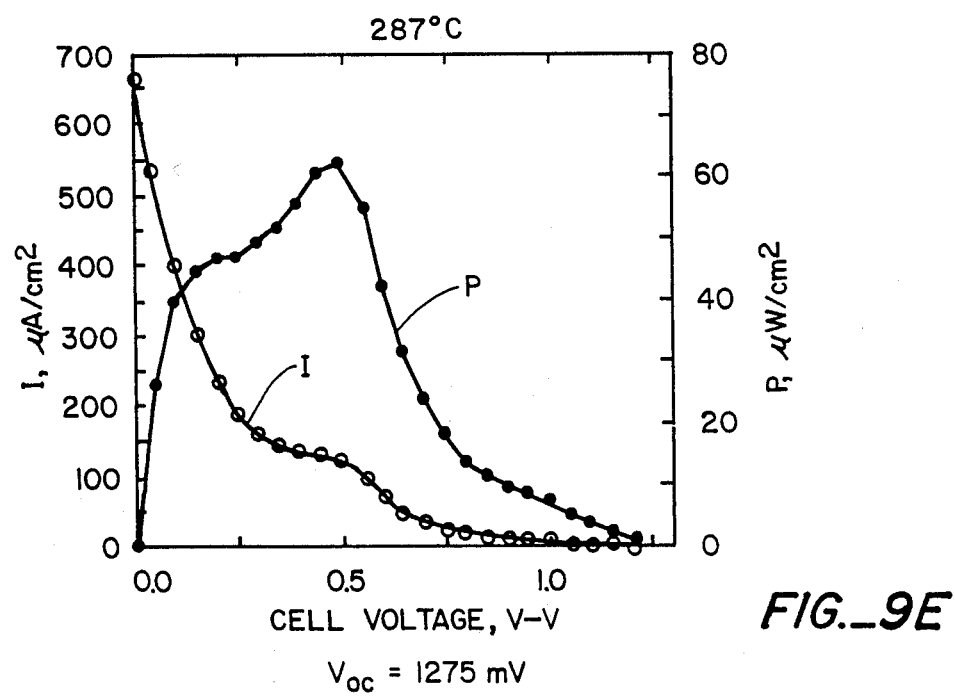
FIG._9E

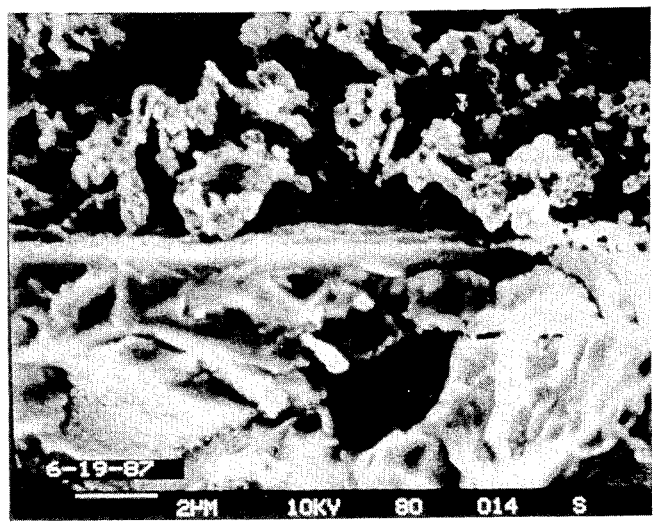
FIG._10
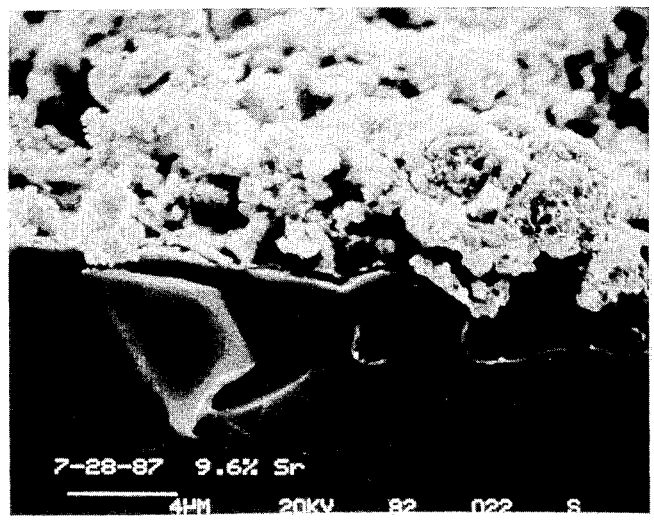
FIG._12

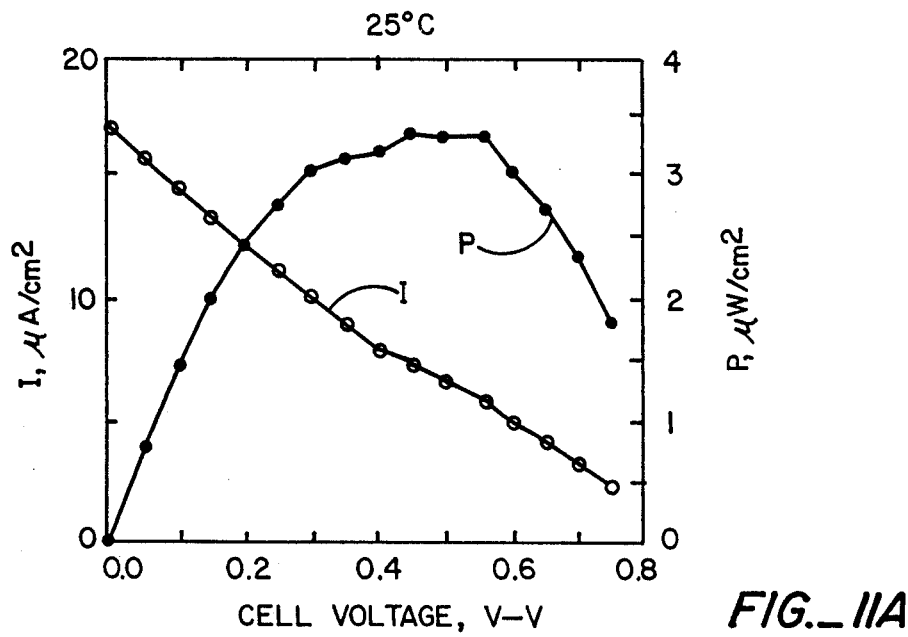
*FIG.__11A*
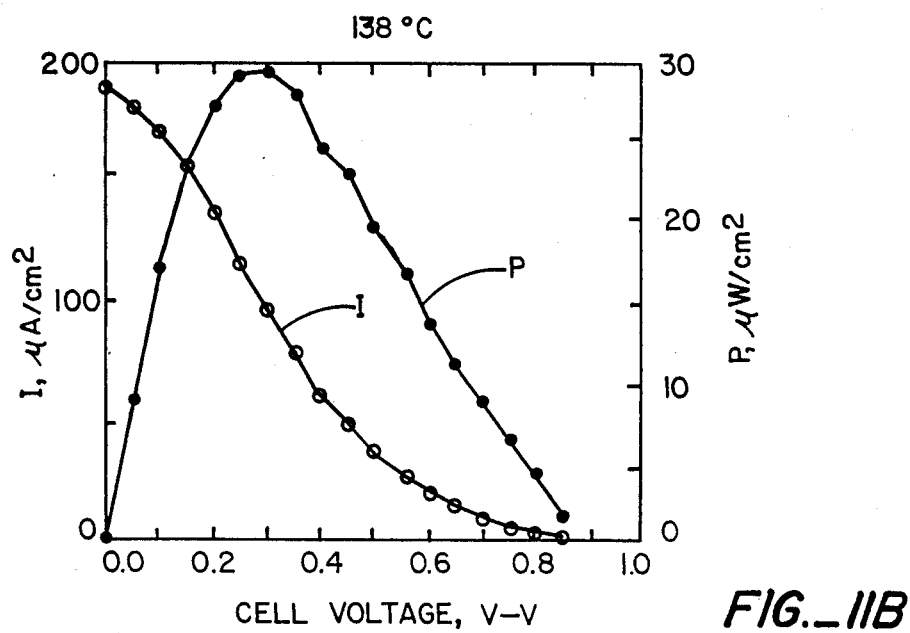
*FIG.__11B*

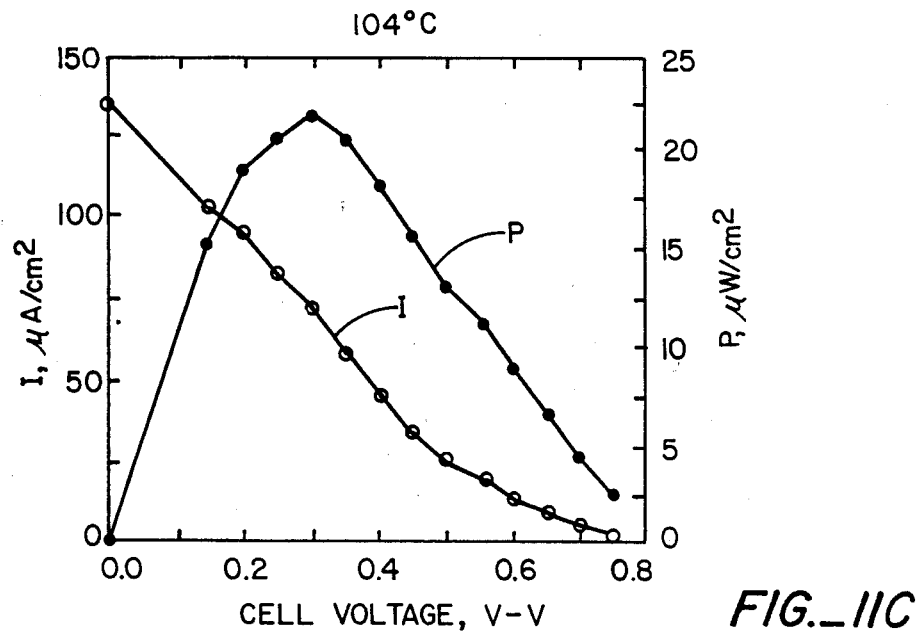
FIG._11C
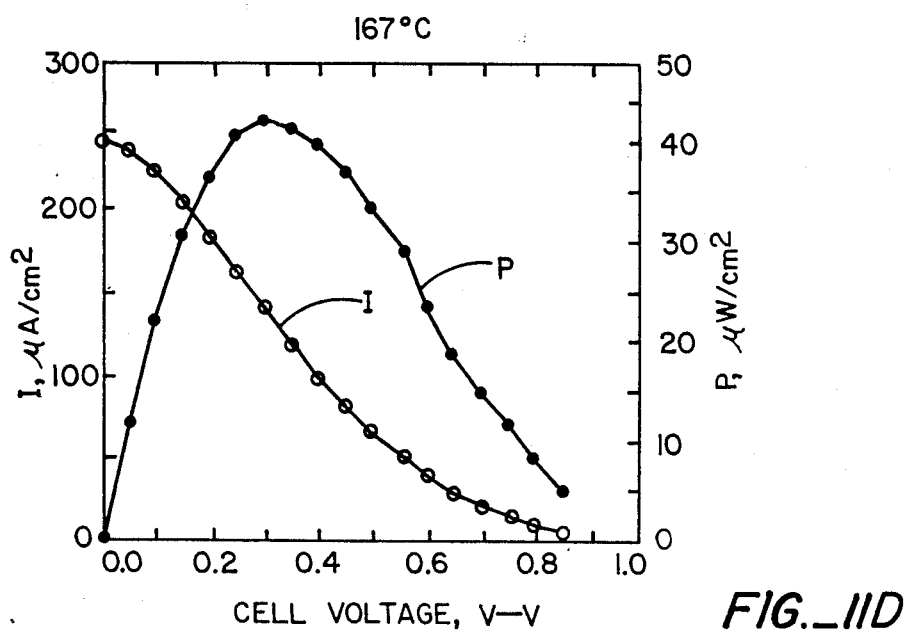
FIG._11D

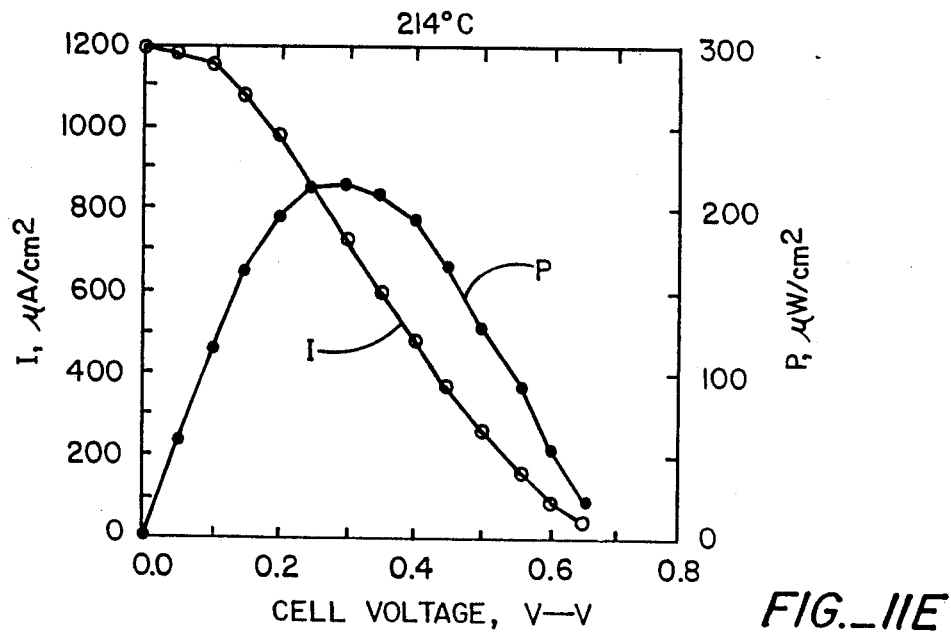
FIG._11E
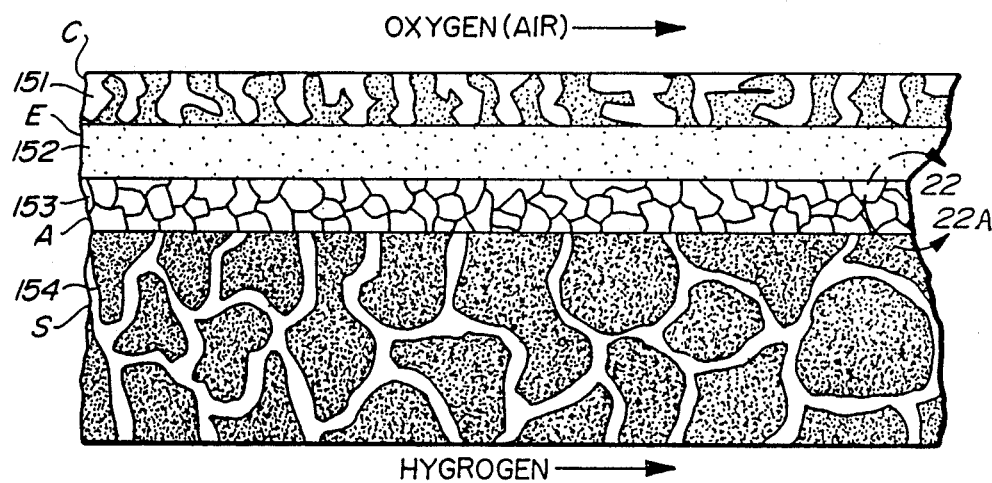
FIG._15

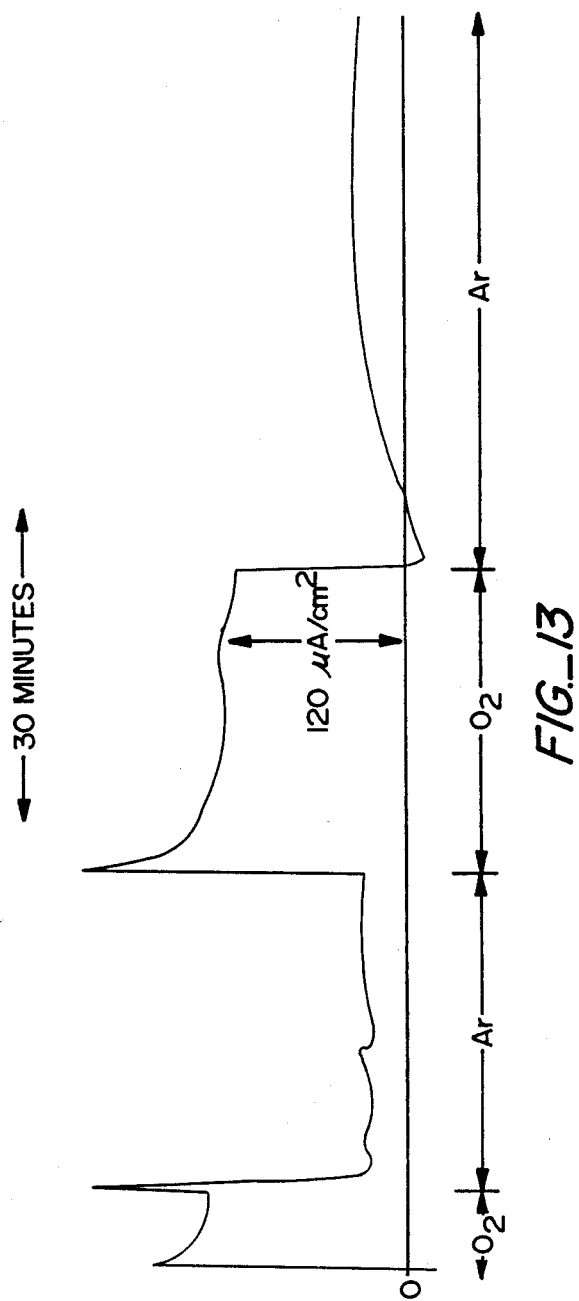
FIG._13

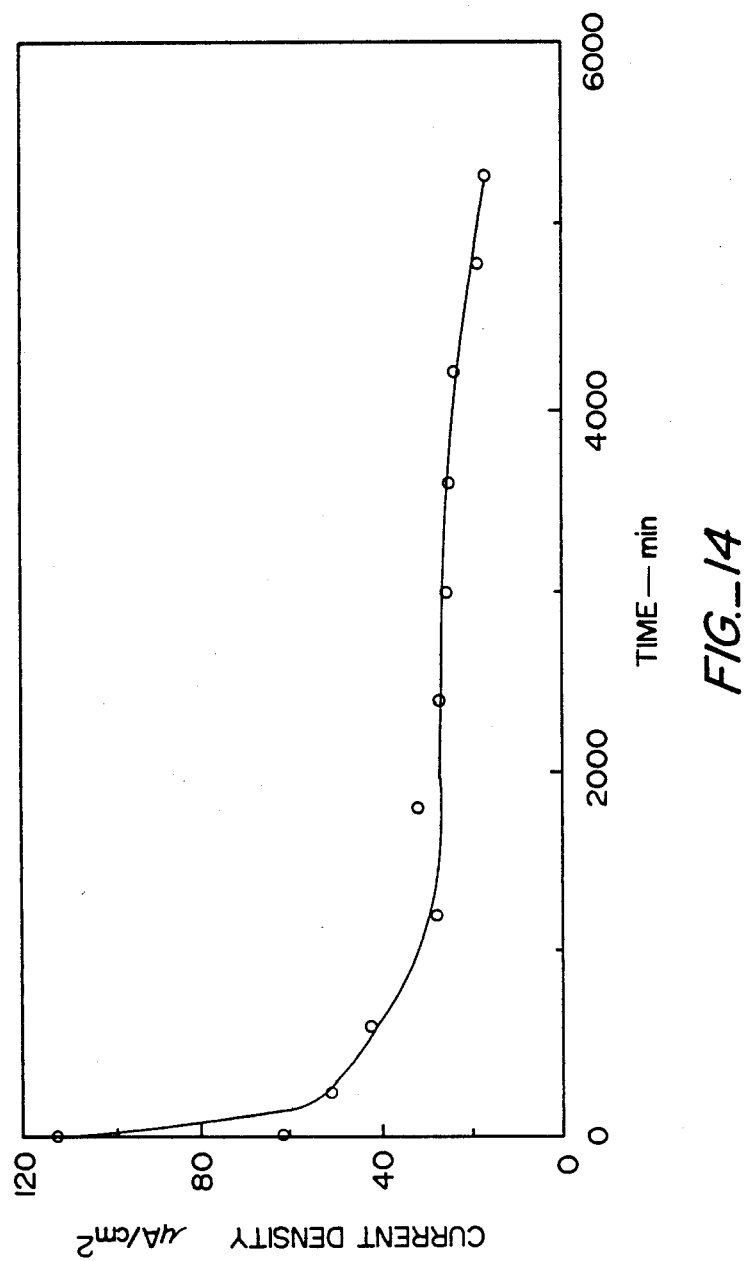
FIG._14

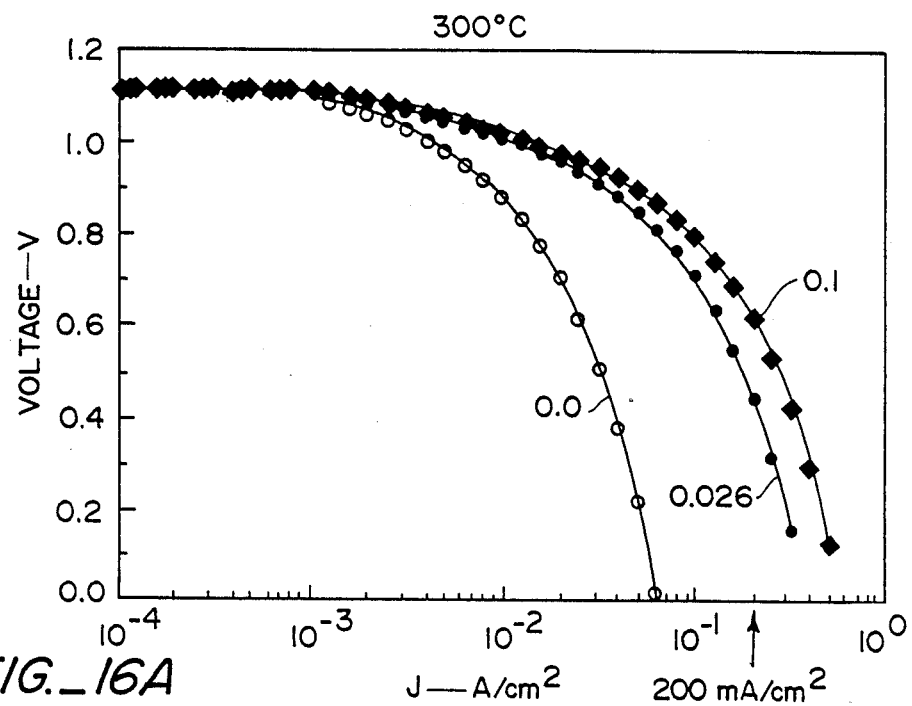
FIG._16A
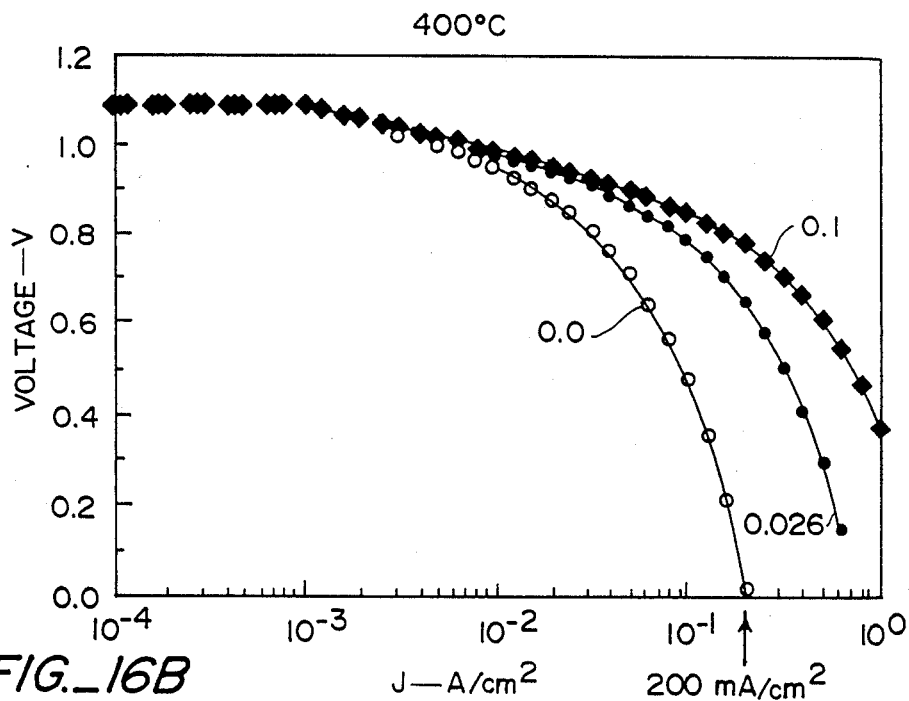
FIG._16B

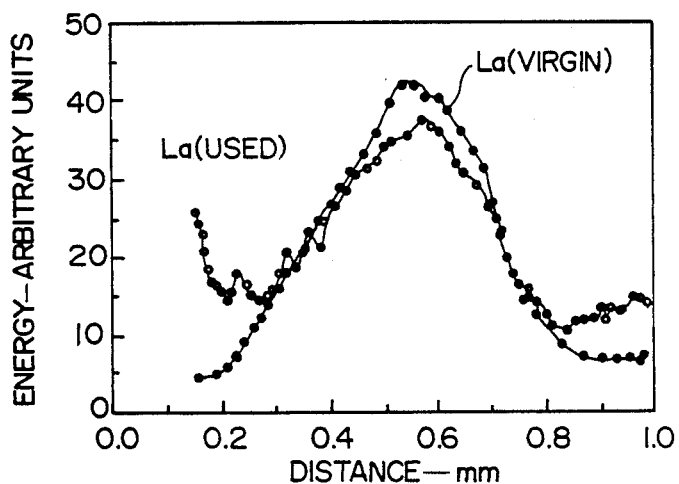
FIG._17A
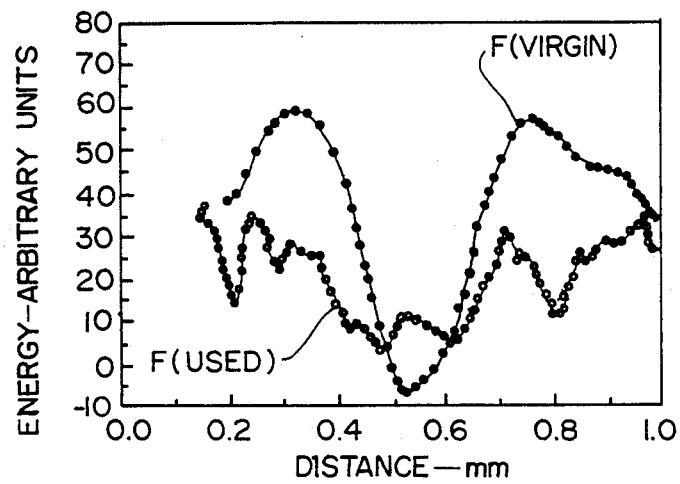
FIG._17B
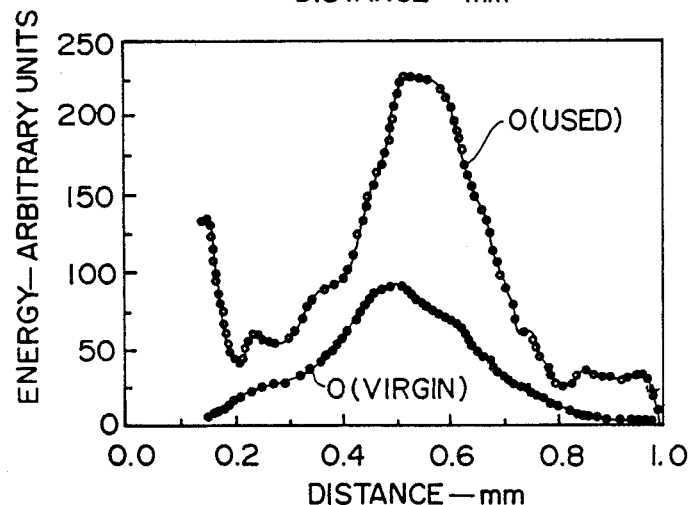
FIG._17C

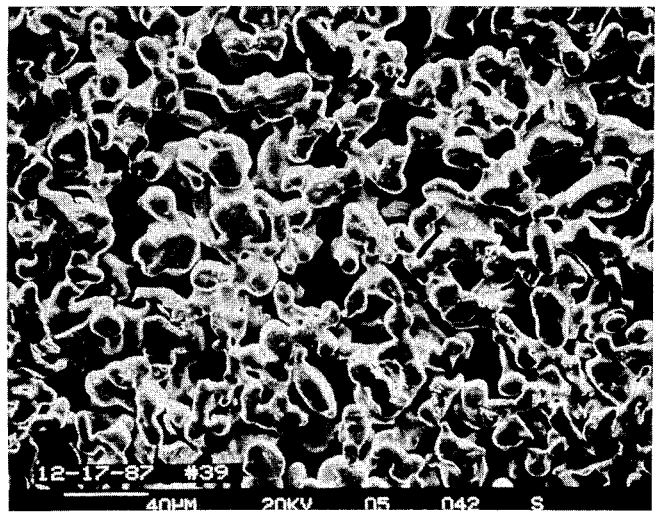
FIG._18A
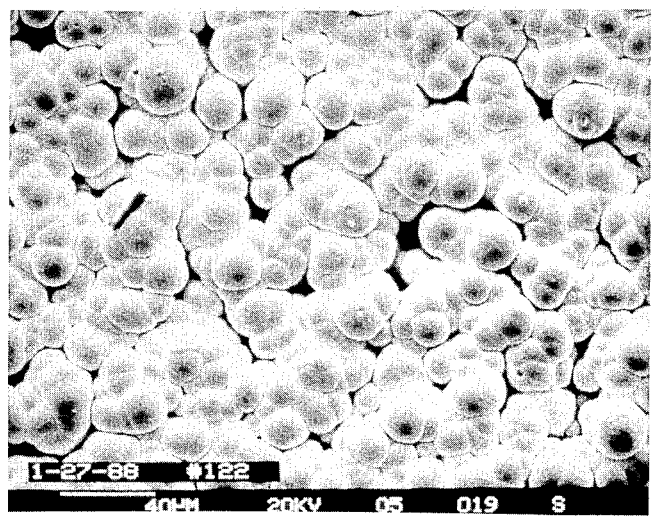
FIG._18B

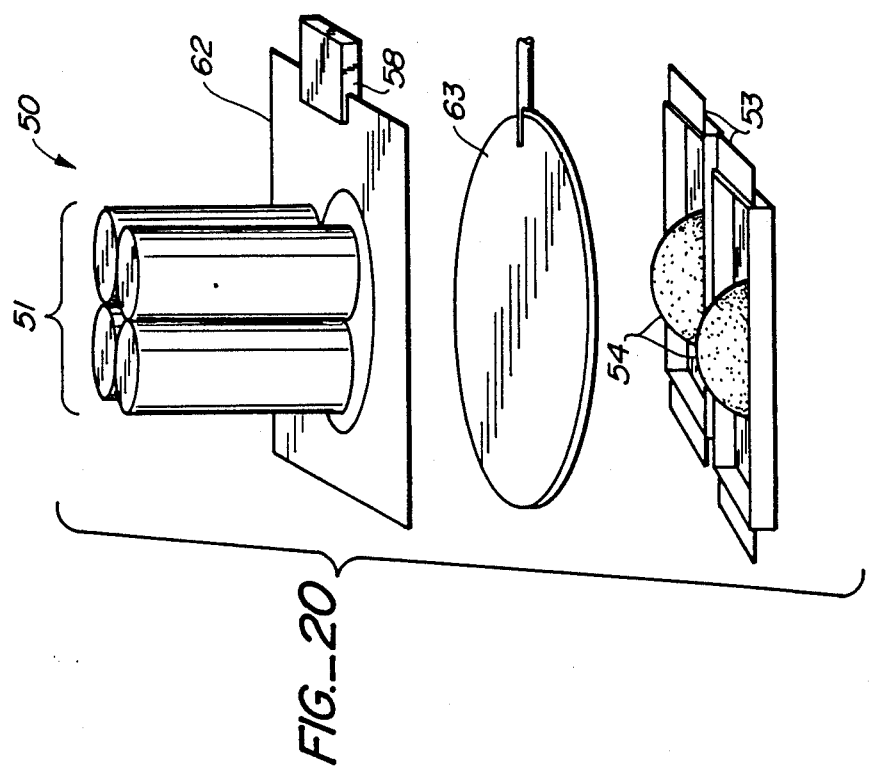
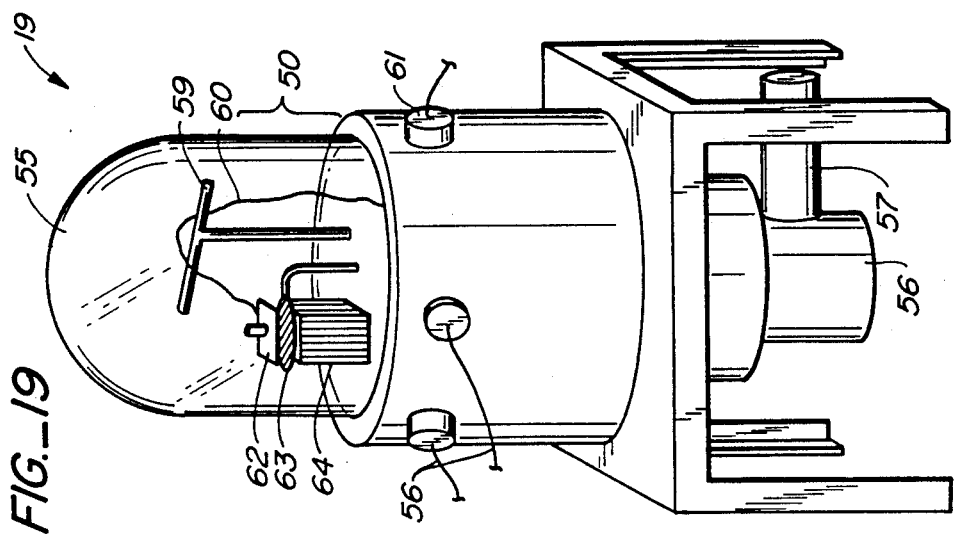

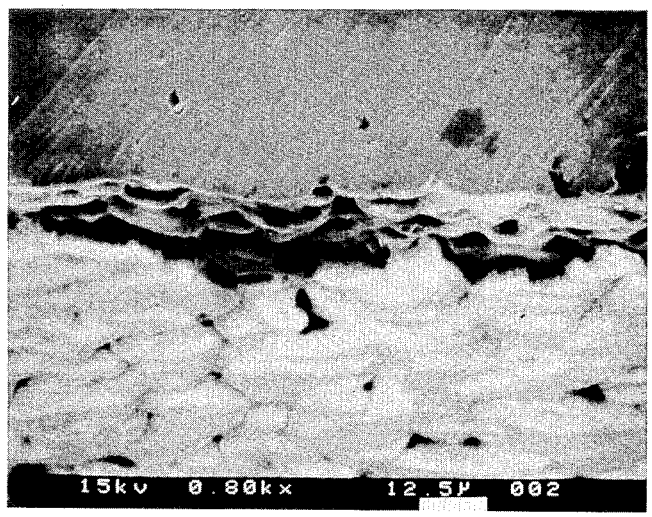
FIG._21

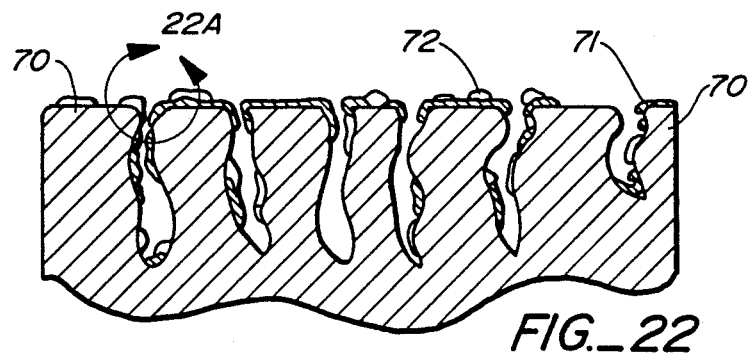
FIG._22
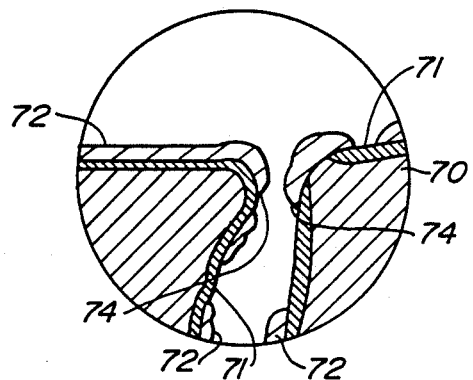
FIG._22A

SOLID COMPOSITIONS FOR FUEL CELL ELECTROLYTES

ORIGIN OF THE INVENTION

The present application is a continuation-in-part of Ser. No. 935,289, filed Nov. 26, 1989, now U.S. Pat. No. 4,851,303, issued July 25, 1989.

BACKGROUND OF THE INVENTION

1. Field of the Invention

The present invention relates to materials and processes to prepare polycrystal and monocrystal forms for use as solid electrolytes in fuel cells. In specific embodiments, a fuel cell having oxygen or air/solid $O^{2-}$ (oxide ion) conducting lanthanum fluoride (as a single crystal) hydrogen configuration produces about 1 volt of open circuit potential at moderately low temperatures. In other specific embodiments, a fuel cell having oxygen or air/specific substituted alkaline earth lanthanide fluorides (either as a single crystal or poly crystal) that conduct $O^{2-}$/hydrogen configuration also produce electricity at moderately low temperatures compared to the present art.

2. Description of the Relevant Art

Fuel cells convert chemical energy to electrical energy directly, without having a Carnot-cycle efficiency limitation, through electrochemical oxidation-reduction reactions of fuels. Several types of fuel cells have been or are being investigated at the present time. These may generally be classified as shown in FIGS. 1A and 1B, as Table 1, depending upon the kinds of electrolyte used and the operation temperature.

The solid electrolyte fuel cell which can be considered as the third generation fuel cell technology, is essentially an oxygen-hydrogen (or $H_2$—CO mixture) fuel cell operated at high temperature (ca. 1000° C.) with a solid ceramic oxide material used as the electrolyte. At present, yttrium- or calcium-stabilized zirconium oxides have been used as the electrolyte. The mechanism of ionic conduction is oxygen ion transport via $O^{2-}$ anion in the solid oxide crystal lattice.

References of interest regarding fuel cells include the following:

B. V. Tilak, R. S. Yeo, and S. Srinivasan (1981), "Electrochemical Energy Conversion-Principals", in "Comprehensive Treatise of Electrochemistry" Vol. 3: Electrochemical Energy Conversion and Storage (J. O'M. Bockris et al., editors), pp. 39-122, Plenum Press, New York.

K. K. Ushiba, (1984), "Fuel Cells", Chemtech, May, pp. 300-307.

A. McDougall (1976), "Fuel Cells", Energy Alternatives Series (C. A. McAuliffe, series editor), The Macmillan Press Ltd., London.

T. Takahashi (1984), "Fuel Cells (Japanese)", Chemistry One Point Series 8 (M. Taniguchi, editor), Kyoritsu-shuppan, Tokyo, Japan.

J. D. Canaday, et al. (1987), "A Polarization Model for Protonic Solid Electrolyte Fuel Cells," *Int. J. Hydrogen Energy*, Vol. 12, No. 3, pp. 151-157.

A. O. Isenberg (1981), "Energy Conversion via Solid Oxide Electrochemical Cells at High Temperatures," *Solid State Ionics*, Vols. 3/4, pp. 431-437.

Additional general information is found in "Fuel Cells" by E. J. Cairns et al. in *Kirk-Othmer: Encyclopedia of Chemical Technology*, (3rd Ed.), Vol. 3, pp. 545-568; and in "Fuel Cells" by O. J. Adlhart in *Van Nostrand's Scientific Encyclopedia*, 6th ed., D. M. Considine (ed), Van Nostrand Reinhold Co., New York, pp. 1296-1299, 1986, which are both incorporated herein by reference.

Lyall in U.S. Pat. No. 3,625,769 and Fouletier in U.S. Pat. No. 4,526,674 each disclose lithium/oxygen fuel cells.

Raleigh in U.S. Pat. No. 4,118,194 and Weininger in U.S. Pat. No. 3,565,692, each disclose halogen electrochemical cells or the like.

Solid electrolyte fuel cells have several advantages over the other types of fuel cells:

1. There are no liquids involved and, hence, the problems associated with pore flooding, maintenance of a stable three-phase interface, and corrosion are totally avoided.

2. Being a pure solid-state device, it poses virtually no maintenance problems. For example, the electrolyte composition is invariant and independent of the composition of the fuel and oxidant streams.

3. Inexpensive metallic oxides (ceramics) rather than expensive platinum can be used as the electrode catalysts.

4. The solid electrolyte fuels cells demand less feed gas preparation than the phosphoric acid cell (see FIG. 1), which requires a conversion of CO to $H_2$ via the water-gas shift reaction, or the molten carbonate cell (see FIG. 1), which requires a carbon dioxide loop due to the use of carbonate ions for ionic transport.

The attraction of developing a solid electrolyte fuel cell is its simplicity. However, a high operation temperature (ca. 1000° C.) is by far the most critical aspect of this type of fuel cell. Although high operation temperature produces high-quality exhaust heat that can generate additional electrical power, leading to a high overall system efficiency, maintaining the integrity of the cell components such as the interconnector is the most difficult challenge.

It is therefore desirable to develop alternative low temperature solid materials and composites for use as solid electrolytes in fuel cells that can be operated in a range of 25°-600° C. or lower (preferably about 200°-400° C., especially at ambient temperature). The present invention relates to the design of such low temperature solid electrolyte fuel cells based on non-oxide solid electrolytes, such as solid solutions of lanthanide fluorides (e.g. $La_{1-x}Sr_xF_{3-x}$).

References of interest regarding such lanthanide fluorides include:

B. C. LaRoy et al., in the *Journal of the Electrochemical Society: Electrochemical Science and Technology*, Vol. 120, No. 12 pp. 1668-1673, published in December 1973, disclose some electrical properties of solid-state electrochemical oxygen sensors using vapor deposited thin films. Polycrystalline thin films of lanthanum fluoride solid electrolytes were investigated at ambient temperature.

In U.S. Pat. Nos. 3,698,955 and 3,719,564, Lilly discloses the use of rare earth fluorides such as lanthanum fluoride as solid electrolytes which are deposited as their films in a battery and a gas sensor respectively.

G. W. Mellors in European Patent Application No. 055,135 discloses a composition which can be used as a solid state electrolyte comprising at least 70 mole percent of cerium trifluoride and/or lanthanum trifluoride an alkaline earth metal compound, e.g. fluoride, and an alkali metal compound, e.g. lithium fluoride.

A. Sher, R. Solomon, K. Lee, and M. W. Muller (1967), "Fluorine Motion in LaF3", in "Lattice Defects and Their Interactions", R. R. Hasiguti, Editor, pp. 363–405, Gordon and Breach Science Publishers, New York.

A. Yamaguchi and T. Matsuo (1981), "Fabrication of Room Temperature Oxygen Sensor Using Solid Electrolyte LaF3 (Japanese)", Keisoku-Jidoseigyo-Gakkai Ronbunshu, Vol. 17(3), pp. 434–439.

M. A. Arnold and M. E. Meyerhoff (1984), "Ion-Selective Electrodes," Anal. Chem., Vol. 56, 20R–48R.

S. Kuwata, N. Miura, N. Yamazoe, and T. Seiyama (1984), "Potentiometric Oxygen Sensor with Fluoride Ion Conductors Operating at Lower-Temperatures (Japanese)", J. Chem. Soc. Japan, 1984(8), pp. 1232–1236, and "Response of A Solid-State Potentiometric Sensor Using LaF3 to A Small Amount of H2 or CO in Air at Lower Temperatures", Chemistry Letters, pp. 1295–1296, 1984.

M. Madou, S. Gaisford, and A. Sher (1986), "A Multifunctional Sensor for Humidity, Temperature, and Oxygen", Proc. of the 2nd International Meeting on Chemical Sensors, Bordeaux, France, pp. 376–379.

N. Yamazoe, N., J. Hisamoto, N. Miura, S. Kuwata (1986), "Solid State Oxygen Sensor Operative at Room Temperature", in Proc. of the 2nd Int. Meeting on Chemical Sensors, Bordeaux, France.

J. Meuldijk, J. and H. W. den Hartog (1983), "Charge Transport in $Sr_{1-x}La_xF_{2+x}$ solid solutions. An Ionic Thermocurrent Study", Physical Review B, 28(2), PP. 1036–1047.

H. W. den Hartog, K. F. Pen, and J. Meuldijk (1983), "Defect Structure and Charge Transport in Solid Solutions $Ba_{1-x}La_xF_{2+x}$", Physical Review B, 28(10), pp. 6031–6040.

J. Schoonman, J., G. Oversluizen, and K. E. D. Wapenaar (1980), "Solid Electrolyte Properties of LaF3", Solid State Ionics, Vol. 1, pp. 211–221.

A. F. Aalders, A. Polman, A. F. M. Arts and H. W. de Wijn (1983), "Fluorine Mobility in $La_{1-x}Ba_xF_{3-x}$ ($0 < x < 0.1$) Studied by Nuclear Magnetic Resonance", Solid State Ionics, Vol. 9 & 10, pp. 539–542.

A. K. Ivanovshits, N. I. Sorokin, P. P. Fedorov, and B. P. Sobolev (1983), "Conductivity of $Sr_{1-x}Ba_xF_{3-x}$ Solid Solutions with Compositions in the Range $0.03 \leq x \leq 0.40$, "Sov. Phys. Solid State, 25(6), pp. 1007–1010.

H. Geiger, et al. (1985), "Ion Conductivity of Single Crystals of the Non-Stoichiometric Tysonite Phase $La_{1-x}Sr_xF_{3-x}$ ($0 \leq x \leq 0.14$)," Solid State Ionics, Vol. 15, pp. 155–158.

A. C. Lilly, et al. (1973), "Transport Properties of La3F Thin Films," J. Electrochem Soc., Vol. 120, No. 12, pp. 1673–1973.

N. Miura, et al. (1987), "Development of Solid State Oxygen Sensor Operation at Room Temperature," Proc. 4th Int. Conf. Solid-State Sensors and Actuators, Toyko, Japan, pp. 681–684 (June).

Some of the structures described herein have been examined for usefulness as battery electrolytes. However, none of the references cited hereinabove, individually or collectively, disclose or suggest the present invention as described herein. All of the references cited above are incorporated herein by reference.

SUMMARY OF THE INVENTION

The present invention relates to a solid $O^{2-}$ (oxide ion) conducting material for use as an electrolyte for a fuel cell, comprising:

(a) a monocrystal or polycrystal structure of the formula:

$$A_{1-x}B_xZ \tag{AA}$$

wherein

A is independently selected from lanthanum, cerium, neodymium, praseodymium, scandium or mixtures thereof;

B is independently selected from strontium, calcium, barium or magnesium, and x is between about 0 and 0.9999, Z is selected from the group consisting of $F_{3-x}$ and $O_cF_d$ where F is fluorine, O is oxygen, x is between about 0 and 0.9999 and $2c + d = 3 - x$, wherein c is between 0.0001 and 1.5 and d is between 0.0001 and less than or equal to 3, with the proviso when A is lanthanum, Z is $F_{3-x}$ and x is 0, the solid material is only a monocrystal.

In another aspect, the present invention relates to a solid electrolyte fuel cell comprising a structure:

$$C-E-A'-S$$

wherein a first electrode material (C), which is only in contact with a thin film solid electrolyte (E) which is also separately in contact with a second electrode material A' which is also separately in contact with a porous mechanical support material (S), wherein the thin film solid electrolyte has the structure:

$$A_{1-x}B_xZ \tag{AA}$$

wherein

A is independently selected from lanthanum, cerium, neodymium, praseodymium, scandium or mixtures thereof;

B is independently selected from strontium, calcium, barium, or magnesium, x is between about 0 and 0.9999, Z is selected from the group consisting of $F_{3-x}$ and $O_cF_d$ where F is fluorine, O is oxygen, x is between about 0 and 0.9999 and $2c + d = 3 - x$, wherein c is between 0.0001 and 1.5 and d is between 0.0001 and less than or equal to 3, with the proviso when A is lanthanum, Z is $F_{3-x}$ and x is 0, the solid material is only a monocrystal.

In a preferred embodiment, the second electrode material is in contact with a porous metallic support (e.g. stainless steel, nickel) that also operates as a current collector.

In yet another aspect the present invention relates to a solid material for use as an electrolyte for a fuel cell comprising:

a monocrystal or polycrystal structure of the formula:

$$Pb_eSn_fF_g$$

wherein

Pb is lead,

Sn is tin,
with the proviso that when f is 1, e is 1 and g is 4 and with the additional proviso that when e is 1, f is 0, and g is 2.

BRIEF DESCRIPTION OF THE DRAWINGS

FIG. 1 (as FIGS. 1A and 1B) shows Table 1 as a comparison of various types of fuel cells.

FIG. 2 shows a representative schematic diagram of the experimental set up to test the solid electrolyte fuel cell.

FIG. 3 shows a representative schematic diagram of the solid electrolyte fuel cell assembly for testing.

FIG. 4 shows a graph of a solid electrolyte fuel cell of dependence of $V_{oc}$ on temperature.

FIG. 5 shows a typical chart recorder response of an open circuit voltage of a single crystal lanthanum fluoride disk upon an On/Off cycle of hydrogen/argon as a function of time.

FIG. 6 (as FIGS. 6A to 6F) shows a set of hydrogen-/oxygen fuel cell current and power vs. cell voltage of single crystal lanthanum fluoride disks (0.64 mm thickness) as a function of temperature and pretreatment with oxygen.

FIG. 7 is a phase diagram of the $SrF_2$–$LaF_3$ system.

FIG. 8 is an X-ray defraction (XRD) pattern from sample with the nominal composition of $La_{0.974}Sr_{0.026}F_{2.974}$.

FIG. 9 (as FIGS. 9A to 9E) shows a set of data concerning the $H_2/O_2$ fuel cell current and power-cell voltage relationship of $La_{0.92}Sr_{0.08}F_{2.92}$ pellets.

FIG. 10 shows a scanning electron micrograph of a cross-sectional view of the platinum catalyst view of the platinum catalyst/polished $La_{0.92}Sr_{0.08}F_{2.92}$ pellet interface.

FIG. 11 (as FIGS. 11A to 11E) shows a set of data concerning $H_2/O_2$ fuel-cell current and power versus cell voltage related to the roughened surface of a $La_{0.904}Sr_{0.096}F_{2.904}$ pellet at five different operating temperatures.

FIG. 12 shows a scanning electron micrographs of a cross-sectional view of the platinum catalyst/roughened $La_{0.904}Sr_{0.096}F_{2.904}$ pellet interface.

FIG. 13 illustrates a typical response of a short-circuit circuit current ($I_{sc}$) of a roughened surface $La_{0.904}Sr_{0.096}F_{2.904}$ pellet (used) as a function of time at approximately 200° C. at an ON/OFF cycle of $H_2/Ar$.

FIG. 14 shows the $I_{sc}$ at 200° C. as a function of time for 100 hours (6,000 minutes) for a pellet of $La_{0.938}Sr_{0.062}F_{2.938}$.

FIG. 15 shows a schematic cross-sectional representation of a thin-film solid-electrolyte fuel cell.

FIGS. 16A and 16B show a graph of the projected performance of a thin film polycrystalline $La_{1-x}Sr_xF_{3-x}$ solid electrolyte fuel cell. FIG. 16A is conducted at 300° C., and FIG. 16B is conducted at 400° C.

FIGS. 17A, B and C show depth profiles of virgin and used polycrystalline $LaF_3$ pellets by Auger electron spectroscopy.

FIG. 18A is a photograph of the original surface of PALL P05 porous stainless steel substrate (0.5 micrometer nominal pore size). FIG. 18B is the surface of the PALL P05 substrate coated with platinum electrochemically deposited at −679 mV for 2.5 hours.

FIG. 19 is an illustration of the vacuum deposition station used to deposit a thin film of $La_{1-x}Sr_xF_{3-x}$ on a porous substrate (e.g., stainless steel).

FIG. 20 is a cut away exploded view of the sample placement within the vacuum deposition station of FIG. 19.

FIG. 21 is a photograph of lanthanum fluoride film (about 10 μm) deposited on an uncoated (i.e. no sample deposition) SSI (S-2930, 2 micrometer nomimal pore size) porous stainless steel substrate.

FIG. 22 is a cross section of a solid material composite useful as a solid electrode having a catalyst support, a platinum contact, a solid coating of an electrolyte (e.g. $La_{0.7}Sr_{0.3}F_{2.7}$) with a solid discontinuous coating of a perovskite-type (e.g. $La_{0.7}Sr_{0.3}CoCO_3$) electrode.

FIG. 22A is an enlarged cross section showing the discontinuous nature of the electrolyte in contact with the electrode on the solid support.

DETAILED DESCRIPTION OF THE INVENTION AND PREFERRED EMBODIMENTS

Definitions

As used herein:

"Contact" refers to the laminate structure of FIG. 15. It refers not only to physical contact but also may refer to a new phase between layer 151 and 152 or between layer 152 and 153 (or i.e., C and E or E and A, respectively), which is produced during formation or afterward having different chemical properties and/or physical properties than the immediately adjacent phase (e.g., a mixed conduction—electron or ion—phase). See FIG. 15 and FIGS. 22 and 22A.

"Fuel gases" refer to oxygen (as defined herein) and hydrogen (as defined herein) or liquids or gases which contain carbon, such as carbon dioxide, carbon monoxide, methane, ethane, natural gas, reformed natural gas or mixtures thereof. Liquids such as methanol, ethanol or mixtures thereof are also useful.

"Hydrogen electrode" or "hydrogen" refers to hydrogen and as used herein may refer to carbon containing fuel gases.

"Oxygen electrode" or "oxygen" refers to the oxidizing electrode side of the fuel cell, and may be oxygen or oxygen mixed with air, or air itself.

In the present invention, $O^{2-}$ (oxide ion) conducting lanthanum fluoride (either in its pure form or its substituted form) is the solid electrolyte of choice for a fuel cell. The basic properties of $LaF_3$ are shown below in Table 2.

TABLE 2

| PROPERTIES OF $LaF_3$ |
|---|
| Crystal structure: hexagonal space group is $P6_3/mcm$ $D^3_{6h}$ with twelve formula units per cell, |
| Melting Point: 1493° C., |
| Density: 5.936, |
| Dielectric constant: 14 (at 10 MHz), |
| Thermal conductivity: 0.025 (W $cm^{-1}deg^{-1}$), |
| Electrical conductivity about $10^{-7}$ $\Omega^{-1}cm^{-1}$ (at 25° C.) |
| Transmits light from the vacuum ultraviolet into the infrared, |
| The effective Debye temperature is: +360° K., |
| The activation energy for fluorine ion diffusion is about 0.45 eV, |
| Activation energy for the formation of defects: about 0.07 eV, |
| Birefringence: n = 0.006, |
| Thermal expansion coefficient: $11 \times 10^{-6}$ cm/cm/°C. (c-axis, 25° C.), a good match is Cu, |

LaF$_3$ has unique physicochemical properties such as high electrical conductivity and high polorizability at room temperature. The Debye temperature of LaF$_3$ is only 360° K., while its melting point is high at 1766° K. The observed phenomena appear to be associated with the formation of Schottky defects and with the activation energy for the diffusion of defects having the unusually low value of about 0.42 eV, and the room temperature Schottky defect density is about $10^{19}/cm^3$.

Fluorine in LaF$_3$ usually exists in three magnetically non-equivalent sites. Covalent bonding predominates in two of the sites. In the third site, the fluorines make up a layered array with approximately 60% ionic bonding and about 40% $\pi$-bonding. The high polarizability and high conductivity of LaF$_3$ at room temperature is primarily due to the motion of F$^-$ ions through the latter sites. The relatively small radius of F$^-$(1.19Å) is almost identical with that of the oxide O$^{2-}$ ion (1.25A); therefore oxide ions (O$^{2-}$ ions) can substitute for the F$^-$ ions in LaF$_3$. The oxygen ion is transported through the bulk of a single crystal LaF$_3$ as measured by Auger electron spectroscopy. In other words, the solid electrolyte LaF$_3$ serves as a supporting electrolyte analogous to liquid phase in which oxygen ions can move freely.

Our solid solutions with the formula $A_{1-x}B_xZ$ (e.g. where A is lanthanum and B is strontium or barium and Z is F and x is defined herein) exhibit a much higher ionic conductivity that pure LaF$_3$. Moreover, this type of solid solution contain a large amount of F$^-$ ion vacancies in which oxygen ions can be sited. Therefore, the solid solutions $A_{1-x}B_xZ$ (where A is lanthanum, B=strontium or barium, Z is F and x is as defined herein) are very attractive as solid electrolytes for lower temperature, solid electrolyte fuel cells.

In practice, Z can also be $O_cF_d$ (where $2c+d=3-x$) due to small impurity oxygen that may be present during the preparation of $A_{1-x}B_xF_{3-x}$. Alternatively, the mobile oxygen ions sitting in the vacant F$^-$ sites may be viewed as $O_cF_d$ instead of pure F or Z (for both monocrystal and polycrystal forms).

Lanthanum Fluoride (Single Crystal) as a Solid Electrolyte for Fuel Cell

Traditionally, LaF$_3$ has been extensively used as a F$^-$ ion selective electrode in electroanalytical chemistry. Recently LaF$_3$ has been applied to a room temperature potentiometric oxygen sensor and to a multifunctional sensor for humidity, temperature, oxygen gas, and dissolved oxygen. However, no disclosure exists concerning the use of LaF$_3$ material as a single crystal as a solid electrolyte in a fuel cell; nor the use of $A_{1-x}B_xZ$ (e.g. $La_{1-x}B_xF_{3-x}$ where $0<x\leqq0.5$) as a single crystal or as a polycrystal for a solid electrolyte in a fuel cell.

Experimental Setup

FIG. 2 depicts a block diagram of the experimental setup 20 used to evaluate various $La_{1-x}B_xF_{3-x}$ solid electrolytes (e.g., single crystal LaF$_3$ disk) for the fuel cell application. The temperature of the cell 21 is maintained at a desired value (about 25°-300° C.) using a heating tape 22 (coiled around the cell), whose voltage is controlled by a transformer. Cell voltages are measured by a high-input impedance electrometer 23 (e.g. Keithley Model 617). A strip chart recorder 26 (e.g., Soltec Model 1243; with three channels) is used to measure currents, cell emf (electromotive forces), or both as a function of time. The measurements are carried out under gentle streams of oxygen 24 (99.99 percent purity) and hydrogen 25 (99.99 percent purity) that are controlled by flowmeters 27A and 27B and are passed through each compartment of the cell at a flow rate of about 20 cc/min. The oxygen may be replaced by air. The hydrogen may be replaced by a fuel gas as defined herein. Current cell-voltage (IV) curves are obtained by controlling the potential difference between two platinum electrodes by means of a PAR Model 173 potentiostat from Princeton Applied Research or a BAS Model CV 37 voltammograph from Bioanalytical Systems. Currents are measured typically 3 min after changing the cell voltages.

Experimental Fuel Assembly

FIG. 3 illustrates the design for the experimental fuel cell assembly 30 in detail. A circle about 4 mm in diameter of Pt mesh 31 (or 31A) (mesh size: 50) is used as a current collector. An ohmic contact is made by mechanically pressing a stainless steel mesh 32 (mesh size: about 60) against the Pt catalyst/Pt mesh using a stainless steel rod 33, which also serves as an electrical lead and is fixed in a rubber stopper 34 (or 34A). A pair of electrode holders made of Teflon (35A, 35B) to hold the disk (e.g., $La_{1-x}Sr_xF_{3-x}$) 36, Pt meshes (30, 30A), and stainless steel meshes (32, 32A) together. A pair of stainless steel tubes 37A, 37B with appropriate gas inlet 38A, 38B and outlet 39A, 39B form the main body of the fuel cell 30. The Teflon electrode holder system (35A and 35B) is inserted between the two stainless steel tubes, and the entire assembly is held together tightly by stainless steel screws 40A, 40B.

Dependence of $V_{oc}$ on Temperature

FIG. 4 graphically presents the open-circuit cell voltages ($V_{oc}$) of a single crystal LaF$_3$ disk 0.64 mm thick as a function of temperature (0° to 300° C.) when the cathode and anode were exposed to oxygen and hydrogen, respectively. The LaF$_3$ disk is equilibrated with each new temperature for about 60 min before a steady-state reading of the $V_{oc}$ was taken. The $V_{oc}$ appears to increase almost linearly with an increase of the cell temperature and saturates around 1.07 V at temperatures about 250° C. The saturated value of 1.07 V obtained is in fair agreement with the theoretical value of $V_{oc}$ for a hydrogen/oxygen fuel cell, i.e. 1.13 V at 227° C. A slight hysteresis was observed in the $V_{oc}$ vs. temperature relation when the measurements are made in the direction of decreasing temperature, indicating that the reaction that determines $V_{oc}$ is not completely reversible.

The large deviation of $V_{oc}$ values from the theoretical values observed at lower temperatures (25° C. to 200° C.), gradually diminishes as the temperature increases. Possible explanations are either that the electrochemical reactions at the electrodes are slow or that the resistance of the solid electrolyte is extremely high (ohmic over potential). An ohmic over potential would most likely be associated with a slow transport of O$^{2-}$ ions in such pure (unpretreated) LaF$_3$ at these low temperatures.

FIG. 5 illustrates a typical response of an open-circuit cell voltage ($V_{oc}$) of an untreated single crystal LaF$_3$ disk as a function of time at about 175° C. When hydrogen is switched to argon in the anodic compartment (while oxygen is passed through the cathodic compartment), the $V_{oc}$ decays to nearly 0 volts within about 10 min; this slow decay is most likely due to residual H$_2$ and H$^+$ ions in the lattice in the vicinity of the anode. The $V_{oc}$ goes back to its original value (about 1 V)

within about 10 seconds upon switching back to hydrogen. The recorder saturated at the point shown by the dotted line. This observation supports the idea that an oxygen/hydrogen fuel-cell reaction is taking place on the single crystal $LaF_3$ disk. These response times become longer as the operating temperature drops.

In the present invention certain combinations of materials, thickness and operating temperatures for the fuel cell are preferred.

In preferred embodiments, the solid material electrolyte described as (AA) in the Summary is one where A is lanthanum, and/or where B is strontium.

In another embodiment, the electrolyte of structure (AA) is one where Z is $F_{3-x}$.

In yet another embodiment, the electrolyte (AA) is one where Z is $O_cF_d$ and where the oxygen is an integral part of the crystal lattice, especially where A is lanthanum, Z is $F_{3-x}$, and x is 0, and the solid material is a monocrystal.

In still another embodiment, the solid material electrolyte (AA) is one where the solid material as a monocrystal has a thickness between about 1 and 300 micrometers, or as a polycrystal has a thickness between about 1 and 100 micrometers.

Preferred temperatures of operation for the fuel cell of structure (AA) to generate an electrical current at a temperature of between about 20° and 600° C., especially between about 200° and 400° C.

Current-Cell Voltage (I-V) Characteristics

FIG. 6 (6A to 6F) presents a set of data concerning the $H_2/O_2$ fuel cell current (I) and power (P) vs. cell voltage relations of a single crystal $LaF_3$ disks 0.64 mm thick with or without a pretreatment as a function of operating temperature. FIGS. 6A, 6C and 6E have no pretreatment. FIGS. 6B, 6D and 6F are pretreated in oxygen at 600° C. for 1 hour. Generally speaking, the electromotive forces (cell voltages) show a good reproducibility, while the current densities do not, probably because of a variation in the morphology of the electrocatalyst/electrolyte interface (i.e., Pt black/$LaF_3$ disk) of each sample.

The current density increases with operating temperature, and the $I_{sc}$ of the $LaF_3$ disk becomes about 20 $\mu A/cm^2$ at 204° C. (see FIG. 6E), which is about 10 times that at room temperature. When the single-crystal $LaF_3$ disks are pretreated by annealing in an oxygen atmosphere for 1 hr at 600° C., current densities increased dramatically. The fuel cell short-circuit current density becomes as high as $2\times10^{-4}$ A/cm² at 206° C. The observed positive influence of the pretreatment of $O_2$ of the $LaF_3$ disk on the current density is most likely due to the formation and/or impregnation of $O^{2-}$ ions into the lattice of $LaF_3$.

In the present invention, certain combinations, material thicknesses of electrolytes, temperature of operation, etc. are preferred. These include the following:

In a preferred embodiment, the solid electrolyte fuel cell is one where the first electrode material is in contact with an oxidizing gas and the second electrode material is in contact with a reducing gas.

In a preferred embodiment, the solid electrolyte fuel cell is one where the anode material is in contact with a reducing gas and the second electrode material is in contact with an oxidizing gas.

In a preferred embodiment, the solid electrolyte fuel cell is one where the porous support is colloidal alumina.

In a preferred embodiment, the solid electrolyte fuel cell is one where the thin film solid electrolyte is between about 1 and 300 micrometers in thickness.

In a preferred embodiment, the solid electrolyte fuel cell is one where in the thin film solid electrolyte B is strontium.

In a preferred embodiment, the solid electrolyte fuel cell is one where in the thin film solid electrolyte A is lanthanum.

In a preferred embodiment, the solid electrolyte fuel cell is one where x is between about 0.001 and 0.2, especially about 0.1.

In a preferred embodiment, the solid electrolyte fuel cell is one where the thin film has a thickness of about 10 micrometers.

In a preferred embodiment, the use of the solid material of claim 1 as an electrolyte (AA) for a fuel cell is conducted at a temperature of between about 200° and 500° C., especially at a temperature of between about 300° to 500° C.

Thermodynamic Considerations

The probable fuel-cell electrochemical reactions taking place at each electrode are: Cathode (positive electrode):

$$O_2 + 4e^- \rightarrow 2\, O^{2-} \tag{1}$$

Anode (negative):

$$2\,H_2 + 2\,O^{2-} \rightarrow 2\,H_2O + 4e^- \tag{2}$$

These lead to the well-known fuel-cell overall reaction: $O_2 + 2H_2 \rightarrow 2\,H_2O$, which has a Gibbs free energy change, $\Delta G°$, of $-56.8$ kcal/mol at room temperature and is thermodynamically very favorable.

In using a $LaF_3$ crystal as a solid electrolyte in a fuel cell, it is reasonable to ask whether or not the formation of HF or $F_2$ is likely in addition to Reaction (2). The thermodynamic considerations governing the formation of these chemical are as follows:

Cathode:

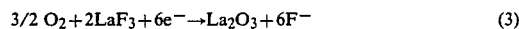
$$3/2\,O_2 + 2LaF_3 + 6e^- \rightarrow La_2O_3 + 6F^- \tag{3}$$

Anode:

$$3H_2 + 6F^- \rightarrow 6HF + 6e^- \tag{4}$$

Overall:

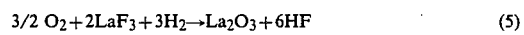
$$3/2\,O_2 + 2LaF_3 + 3H_2 \rightarrow La_2O_3 + 6HF \tag{5}$$

$$\Delta G° = +40.2 \text{ kcal/mol at 25° C.}$$

Cathode:

$$3/2\,O_2 + 2LaF_3 + 6e^- \rightarrow La_2O_3 + 6F^- \tag{3}$$

Anode:

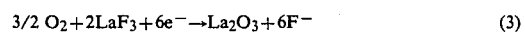
$$6F^- \rightarrow 3F_2 + 6e^- \tag{6}$$

Overall:

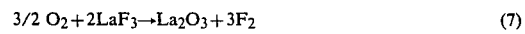
$$3/2\,O_2 + 2LaF_3 \rightarrow La_2O_3 + 3F_2 \tag{7}$$

$$\Delta G° = +432 \text{ kcal/mol at 25° C.}$$

Therefore, Reactions (5) and (7) above, are thermodynamically unfavorable and quite unlikely. It is noted, however, that the product of the cathodic reaction in Eq. (3) may be a lanthanum oxyfluoride that can be written as $LaO_xF_{3-2x}$ (for which no thermodynamic data are available), rather than $La_2O_3$ (at least at the $LaF_3$ surface). It is likely that the formation of $LaO_xF_{3-2x}$ is thermodynamically more favored than that of $La_2O_3$, which might lead to the production of a very small amount of HF.

Polycrystalline $La_{1-x}B_xF_{3-x}$ Materials

The basic method we have chosen for preparing polycrystalline pellets is as follows:

Mix $LaCl_3.7H_2O$ and $SrCl_2.6H_2O$
Dissolve mixture in dilute HCl
Add HF solution for coprecipitation
Decant and settle (three times)
Filter
Dry at about 120° C. (overnight)
Calcinate (overnight at about 950° C. in argon)
Press and sinter (hot press)

Coprecipitation of the fluorides form a slightly acidic solution of the chlorides is the most efficient means of ensuring a homogeneous mixture. The salts are dissolved in deionized water with a small amount of HCl added to ensure that the pH is sufficiently low as to prevent formation of the insoluble hydroxides. A commercial $NH_4F$:HF solution with a ratio of 7:1, sold to the semiconductor industry as buffered oxide etch (BOE), has been used as the precipitant because it is the most chemically pure fluoride source available; in addition, because it is buffered, it is less hazardous than pure HF. See Example 7. The resulting power samples of $La_{1-x}B_xF_{3-x}$ (B=strontium or barium) as pressed into rods (approximately 1 cm in diameter by approximately 2 cm long) by conventional hot-pressing process. Individual pellets with approximately 1 mm thickness are prepared by slicing the rods using a mechanical saw. Alternatively, some of the powders are first pressed hydrostatically into disks, which are subsequently sintered.

A phase diagram of the system $SrF_2$—$LaF_3$ is presented in FIG. 7 (Yoshimoto, Kim and Somiya, 1985, 1986), together with our data points (shown as solid or open diamonds). According to this phase diagram, solubility limits in the system $SrF_2$—$LaF_3$ to form a single phase solid solution are a function of temperature as follows:

| Temperature (°C.) | $LaF_3$ in $SrF_2$ (mol-%) | $SrF_2$ in $LaF_3$ (mol-%) |
|---|---|---|
| 1400 | 48 | 15 |
| 1000 | 48 | 11 |
| 750 | 47 | 6 |
| 650 | 47 | 4 |
| 500 | 46 | 2 |

Therefore, one is able to synthesize single-phase $A_{1-x}B_xF_{3-x}$ solid solutions using temperatures below 1400° C. only when strontium concentrations are below 15 percent.

FIG. 8 is an XRD pattern from a sample with the nominal composition of $La_{0.974}Sr_{0.026}F_{2.974}$, which is single phase, showing a substantially identical XRD pattern as the one for $LaF_3$. However, there is a very small peak at about d=3.35Å, indicated by the arrow in FIG. 8, which is most probably due to LaOF.

The formation of a single phase with minor peak due to the presence of LaOF is confirmed with polycrystalline strontium (or barium) substituted (i.e. B is strontium or barium) substituted $A_{1-x}B_xF_{3-x}$ pellets in the range where x is greater than or equal to 0 and less than or equal to 0.15.

Fuel Cell Performance Data Obtained with
$La_{1-x}M_xF_{3-x}$ Polycrystalline Pellets FIG. 9 (9A to 9E) presents a set of data concerning the $H_2/O_2$ fuel cell current (I) and power (P) cell voltage relations of $La_{0.92}Sr_{0.08}F_{2.92}$ pellets (approximately 1 mm thick) with and without a physical pretreatment of polishing both sides of the pellets by an emery paper (#120) as a function of operating temperature. (FIGS. 9A and 9C are as prepared; FIGS. 9B, 9D and 9E are polished). The polished pellet with the surface layer removed by polishing gives a much higher current density (by about a factor of 10) than the unpolished pellet with as-prepared surface. The observed increase of reaction rate (i.e. current density) of the fuel cell is due to an increase the "real" electrochemical surface area, i.e. number of the triple contact points, where the gas reactions can take place.

A scanning electron micrograph (SEM) of a cross-sectional view of the platinum catalyst/polished $La_{0.92}Sr_{0.08}F_{2.92}$ pellet interface is shown in FIG. 10. An array of submicron-size "ridges" is visible at the platinum/solid electrolyte interface. The observed enhancement of $I_{sc}$ on the polished surface could be also partly due to the removal of the surface layer that may contain some "undesirable" materials (e.g. LaOF). It therefore would be still possible to enhance the current density further, say by another factor of 10, by carefully optimizing the microstructure of the interface.

The effect of operation temperature was studied using the same polished $La_{0.92}Sr_{0.08}F_{2.92}$ pellet. When the temperature was increased from 215° C. to 287° C., the short-circuit current density was increased: from 165 $\mu A/cm^2$ to 674 $\mu A/cm^2$ i.e., a factor of 4. An almost linear decrease of the current density with the cell voltage in the low cell voltage region of the I-V plot at 287° C. is indicative of a high electrolyte resistance (a total of approximately 400Ω) still existing at this temperature. This situation can be improved by making the electrolyte much thinner.

High current density is observed with an approximately 2-mm thick $La_{0.904}Sr_{0.096}F_{2.904}$ pellet with a roughened surface, which produced approximately 1.2 $mA/cm^2$ at 214° C. This value should be compared with the performance of a typical hydrogen/oxygen solid electrolyte fuel cell based on (for example) a calcia-stablized zirconia $(ZrO_2)_{0.85}(CaO)_{0.15}$ 0.4 mm thick, which exhibit an $I_{sc}$ of approximately 60 $mA/cm^2$ at 900° C. (McDougall, 1976). FIG. 11 (11A to 11E) presents a set of data concerning $H_2/O_2$ fuel-cell current and power vs. cell voltage relations of the roughened surface $La_{0.904}Sr_{0.096}F_{2.904}$ pellet at five different operating temperatures. Two thin layers of commercial fuel-cell grade platinum black power, which serve as "grinding" powder, are first pressed together with powder of the electrolyte placed in between. The platinum black came off after sintering, and the platinum catalyst is applied using $H_2PtCl_6$ solution. A scanning electron micrograph of a cross-sectional view of the platinum catalyst/roughened $La_{0.904}Sr_{0.096}F_{2.904}$ pellet interface is shown in FIG. 12. Indeed, the interface presents a very rough surface on which highly porous platinum catalysts are densely deposited and uniformly distributed over the surface with few voids.

The same magnitude of high current density (on the order of 1 mA/cm$^2$) was also observed when a composite was used as an electrode; a 50%/50% mixture by weight of the platinum black powder catalyst and the powder of $La_{0.904}Sr_{0.096}F_{2.904}$ were pressed and inserted together with the electrolyte powder of $La_{0.904}Sr_{0.096}F_{2.904}$ in between, and used as an electrode. In conclusion, a further improvement of current densities by one or two orders of magnitude should be possible when an ultra-thin film of $La_{1-x}Sr_xF_{3-x}$ is used in conjunction with proper electrocatalysts and an optimized electrolyte/electrode interface.

FIG. 13 illustrates a typical response of a short-circuit current ($I_{sc}$) of a roughened surface $La_{0.904}Sr_{0.096}F_{2.904}$ pelled (used) as a function of time at approximately 200° C. When oxygen is switched to argon in the cathodic compartment (while hydrogen is passed through the anodic compartment), the $I_{sc}$ rapidly decays to around 0 within 20 s. The $I_{sc}$ goes back to its original value within 20 s upon switching back to oxygen. This observation strongly supports the observation that an oxygen/hydrogen fuel-cell reaction is taking place on the pellet of $La_{0.904}Sr_{0.096}F_{2.904}$. The residual current observed in argon is most likely due to oxide ions ($O^{2-}$) remaining in the lattice.

A long term "fuel-cell" performance test was carried out at approximately 200° C. using a pellet of $La_{0.904}Sr_{0.096}F_{2.904}$, which was pretreated in oxygen at 600° C. for 20 hours. FIG. 14 shows the $I_{sc}$ as a function of time for 100 hr. (6000 minutes); as observed with the $LaF_3$ single crystal disk the $I_{sc}$ gradually decreased and became a quasi-steady state. The precise mechanism for this degradation is not fully understood. It would be reasonable to attribute a part of this degradation to a gradual deterioration of the morphological stability of the catalyst/solid electrolyte interface under the operating conditions. However, our independent experimental data suggests that the degradation could be, to a larger extent, due to rather "poor" gas sealing conditions provided by the Teflon electrolyte holder/gasket.

Thin-Film Polycrystalline $La_{1-x}Sr_xF_{3-x}$ Solid Electrolyte Fuel Cell

FIG. 15 shows an idealized schematic cross section of a laminate of a thin-film $La_{1-x}Sr_xF_{3-x}$ solid-electrolyte fuel cell. The cell is arranged in a multilayer structure on a porous support 154. A similar basic structure but on a porous support "tube" has been used for Westinghouse thin-film zirconia solid-electrolyte fuel cell (Isenberg, 1981). The porous support 154, such as porous sintered glass (e.g. Vycor glass) and porous alumina, provides mechanical integrity for the multilayer structure and also serves as conduit for one of the reactants, e.g. hydrogen. Alternatively, an electronically conductive (e.g., metallic substrate such as porous stainless steel or a nickel disk and porous sintered nickel plaque) could be used as the mechanical support 154 which also serves as a current collector, and as an electrocatalyst (e.g. nickel).

FIG. 15 shows cathode (C) as 151, electrolyte (E) as 152, anode (A) as 153 and support (S) as 154. The anode A and cathode (C) may be reversed when the gases $O_2$ and $H_2$ are also reversed.

FIGS. 22 and 22A present a more realistic view of the discontinuous surface of the solid electrolyte fuel cell of FIG. 15. FIG. 22 shows the configuration of a supported composite for use in a fuel cell. The perovskite substrate 71 is spray dried onto an inorganic or metal support 70 (or 154) such as silica, thoria, zirconia, magnesia, stainless steel or the like having mechanical stability. The fluoride electrolyte (E) 72 is then vapor deposited on the surface of the perovskite 71. As shown in FIG. 22A the fluoride electrolyte 72 as a vapor enters the pores of the perovskite 71 and the substrate 70 in a discontinuous manner. In this way, millions of two-material catalytic surfaces 74 are created to facilitate the electrochemical reaction at the intersection of the perovskite 71 and fluoride 72.

The overall performances of the low-temperature thin-film $La_{1-x}Sr_xF_{3-x}$ solid-electrolyte fuel cell are reasonably predicted as follows using a mathematical overall cell voltage, $V_{cell}$/current density, J, relation (Canady et al.; 1987):

$$V_{cell} = V^\circ - \frac{RT}{2F} \ln\left(\frac{J_{L,a}}{J_{L,a} - J}\right) - \frac{RT}{2F} \ln\left(\frac{J}{J_{o,a}}\right) - \frac{RT}{4F} \ln\left(\frac{J_{L,c}}{J_{L,c} - J}\right) - \frac{RT}{4F} \ln\left(\frac{J}{J_{o,c}}\right) - \rho LJ, \quad (8)$$

where V° is the reversible thermodynamic electromotive force (emf), R is gas constant, T is absolute temperature, F is Faraday's constant, L is electrolyte thickness, is the specific resistance of the solid electrolyte, $J_{L,a}$ and $J_{L,c}$ are limiting current densities at anode and at cathode, and $J_{o,a}$ and $J_{o,c}$ are exchange current densities at anode and cathode, respectively. The second and fourth terms in Eq. (8) represent the concentration polarization of the electrodes (which depends on the electrode morphological parameters, porosity and thickness); the third and fifth terms in Eq. (8) represent activation polarization at the three-phase point of the electrode-electrolyte interface, and the last (sixth) term in Eq. (8) represents ohmic polarization (which solely depends on electrolyte resistivity and thickness).

Table 3 lists values of thermodynamic emf and resistively used in the calculations. In these calculations, values are used (as a first approximation) for exchange current density for electrodes $J_{o,a}$ and $J_{o,c}$, data that were experimentally determined for the case of zirconia-and ceria-based fuel cells, viz. approximately 1 mA/cm$^2$ for both electrodes (Canaday, et al., 1987). The anode and cathode limiting current densities, $J_{L,a}$ and $J_{L,c}$, associated with an interdiffusion of hydrogen and oxygen, have been estimated as 82.9 and 44.3 A/cm$^2$ at 300° C. and 1 atm, respectively, assuming bulk electrode thickness of 10 μm with a porosity of 10 percent (Canaday, et al., 1987).

TABLE 3

| | THERMODYNAMIC EMF AND RESISTIVITY | | |
|---|---|---|---|
| Operating Temperature (°C.) | Thermo-dynamic emf (V)* | Strontium Concentration (mol-percent) | Resistivity of Polystalline $La_{1-x}Sr_xF_{3-x}$ Films (Ω-cm) |
| 200 | 1.143 | 0 | 97200 |
| | | 0.026 | 7650 |
| | | 0.1 | 9720 |
| 300 | 1.121 | 0 | 15100 |
| | | 0.026 | 2350 |

TABLE 3-continued
THERMODYNAMIC EMF AND RESISTIVITY

| Operating Temperature (°C.) | Thermodynamic emf (V)* | Strontium Concentration (mol-percent) | Resistivity of Polystalline $La_{1-x}Sr_xF_{3-x}$ Films (Ω-cm) |
|---|---|---|---|
| 400 | 1.090 | 0.1 | 1510 |
|  |  | 0 | 4190 |
|  |  | 0.026 | 1060 |
|  |  | 0.1 | 419 |
| 500 | 1.062 | 0 | 1650 |
|  |  | 0.026 | 595 |
|  |  | 0.1 | 165 |

*Tilak, Yeo, and Srinivasan, 1981.
Estimated, assuming that the resistivity of polycrystalline $La_{1-x}Sr_xF_{3-x}$ thin films is two orders of magnitude greater than the resistivity of the single crystals (Gieger, Schon, and Stork, 1985; Lilly et al., 1973).

FIGS. 16A and 16B show the calculated cell voltages plotted against current density (I-V curves) for the polycrystalline films of $La_{1-x}Sr_xF_{3-x}$ as a function of operating temperature (300° and 400° C.) for the film thickness 10 μm; in each case, three different concentrations of strontium substitution (viz. x=0, 0.026, and 0.1) are considered. When the $LaF_3$ polycrystals are doped with strontium (2.6 or 10 mol-percent), a cell voltage of approximately 0.6 V or 0.8 V is found, which generates a current density of 200 mA/cm² when the fuel cell is operated at 300° C. or 400° C., respectively. The effect of strontium concentration (x=0.026 or 0.1) appears to be minimal. Similar performance levels may be obtained by highly nonstoichiometric films of $LaF_{3-x}$ (made by e.g., electron-beam evaporation) that exhibit comparable ionic conductivity. A further increase in operating temperature to 500° C. does not seem to improve the fuel-cell performance in terms of the I-V curves, so long as the strontium concentration is maintained between 2.6 and 10 mol-percent. On the other hand, the fuel-cell maximum power density dramatically increases almost linearly with an increase of operating temperature; especially when the strontium content is 10 mol-percent, and reaches approximately 0.55 W/cm² at 500° C.

The set of I-V curves shown in FIG. 16A and 16B may represent rather a modest case, because the calculations were made on the basis of highly resistive polycrystalline $La_{1-x}Sr_xF_{3-x}$ films [it was assumed that the resistivity of polycrystalline $La_{1-x}Sr_xF_{3-x}$ thin films is two orders of magnitude greater than the resistivity of the single crystal, following the data given by Lilly et al. (1983) on thin films of $LaF_3$]. Fuel-cell performance could be further significantly improved if we could reduce the resistivity of polycrystalline films by carefully optimizing a thin-film deposition process. For example, if the resistivity of polycrystalline $La_{1-x}Sr_xF_{3-x}$ films is reduced by two orders of magnitude (thus approaching the resistivity values of single crystals), a cell voltage of approximately 0.9 V (which generates a current density of 200 mA/cm²) can be obtained by 10-μm thick $La_{1-x}Sr_xF_{3-x}$ films with x=0, 0.026, or 0.1 at only 300° C.

Thin Film Deposition Techniques

Table 4 compares three physical thin-film deposition techniques that might be used to fabricate thin films (e.g. 5 to 50-μm (preferred 5 to 15 μm) thick of polycrystalline $La_{1-x}Sr_xF_{3-x}$ for the fuel-cell application.

TABLE 4
CANDIDATE THIN-FILM DEPOSITION TECHNIQUES FOR POLYCRYSTALLINE $La_{1-x}Sr_xF_{3-x}$

| Technique | Starting Materials | Typical Conditions | Deposition Rate | Comments |
|---|---|---|---|---|
| Magnetron sputtering | Powder (or single crystals) | Argon atmosphere ($\approx 4 \times 10^{-2}$ torr) | $\approx 0.25$ μm/h* |  |
| Thermal evaporation | Powder (or single crystals) | Ultrahigh vacuum ($\approx 10^{-7}$ torr); substrate 200 to 300° C. | $\approx 1$ μm/h | Stochiometric $LaF_3$ film |
| Electron-beam evaporation | Powder (or single crystals) | Ultrahigh vacuum ($<10^{-6}$ torr); substrate 500° C.; e-gun 10 kV, 500 mA | $>1$ μm/h | Nonstochiometric $LaF_{3-x}$ film |

*Miura et al. (1987)
Laroy et al. (1973)

In vacuum evaporation—the best established thin-film deposition process for $LaF_3$—the source compound is evaporated by heating with a thermal or electron-beam heater and deposited on the substrate. Areas are delineated either by a shadow mask or by photolithography. Electron beam evaporation is a particularly attractive method for depositing polycrystalline $La_{1-x}Sr_xF_{3-x}$ films for the fuel-cell application, because the film deposition rate can be as fast as 10 μm/h and highly nonstoichiometric, conductive films of $LaF_{3-x}$ (for which strontium-doping might not be necessary) can be formed.

Magnetron sputtering is a process that is similar to (but faster than) diode sputtering and is primarily useful for films that are thicker than 5 μm. However, the film deposition rate of magnetron sputtering is still slower than vacuum evaporation methods.

In addition to the physical methods described above, chemical processes, such as chemical vapor deposition and screen printing, may be used to prepare thin films of polycrystalline $La_{1-x}Sr_xF_{3-x}$ films. Screen printing is widely used in electronic manufacturing (e.g. ceramic capacitors). Screen-printed deposits are thicker than sputtered and evaporated layers, usually in the range of 10 to 50 μm. The deposits are made from a paint-like suspension of particles and binders that, after application through a patterned screen, are dried and sintered to form a coherent (but often porous) mass. The resultant deposit can be similar to the pressed materials. Screen printing is particularly suited for volume production techniques, because manufacturing equipment is available and printing precision is relatively high. However, it is expected that this method is applicable to the deposition of polycrystalline $LaF_{3-x}$ or $La_{1-x}Sr_xF_{3-x}$ films.

Plasma enhanced chemical vapor deposition (PECVD) uses an RF glow discharge to generate highly reactive species, and is attractive for a large-scale production, although PECVD has not been used to fabricate $LaF_{3-x}$ or $La_{1-x}Sr_xF_{3-x}$ films.

In another aspect, the present invention relates to a process [BB] for preparing a composite comprising:

$$A_{1-x}B_xQO_3$$

having a perovskite or perovskite-type structure as an electrode catalyst in combination with:

$$A_{1-x}B_xZ$$

as a discontinuous polycrystalline surface coating solid electrolyte wherein

A is independently selected from lanthanum, cerium, neodymium, praseodymium, or scandium, B is independently selected from strontium, calcium, barium or magnesium, Q is independently selected from nickel, cobalt, iron or manganese, and x is between about 0 and 0.9999, Z is selected from the group consisting of $F_{3-x}$ and $O_cF_d$ where F is fluorine, O is oxygen, x is between about 0 and 0.9999 and $2c+d=3-x$, wherein c is between 0.0001 and 1.5 and d is between 0.0001 and less than or equal to 3, which process comprises:

(a) obtaining a particulate of:

$$A_{1-x}B_xQO_3$$

wherein A, B, Z and x are defined hereinabove, having an average crystal size distribution of between about 50 and 200 Angstroms in diameter and a surface area of between about 10 and 100 meters 2/grams and formed into a film-like or pellet-like shape having a general thickness of between about 1 and 5 mm, a pore size of between about 25 and 200 Angstrom; and (b) reacting the particulate of step (a) with a vapor comprising:

$$A_{1-x}B_xZ$$

wherein A, B, Z and x are defined hereinabove, at about ambient pressure at between about 0° and 1000° C.: for between about 10 and 30 hr. obtain the composite of between 25 to 1000 microns in thickness; and (c) recovering the composite of step (b) having multiple interfaces between:

$$A_{1-x}B_xQO_3 \text{ and } A_{1-x}B_xZ$$

said composite having a pore size of between about 25 and 200 Angstroms and a surface area of between about 10 and 100 meters²/gram.

A preferred embodiment in this process [BB] is wherein A is lanthanum, B is strontium, Q is cobalt, and especially where x is about 0.3. Another preferred embodiment of process [BB] is wherein A is selected from cerium or scandium, B is selected from strontium or magnesium, Q is selected from nickel, cobalt or manganese and x is between about 0.2 and 0.4.

The perovskites useful in this invention may be purchased or may be formed according to the procedures described in the literature, e.g., T. Kudo, et al., U.S. Pat. No. 3,804,674, which is incorporated herein by reference.

The following Examples are meant to be illustrative and descriptive only. They are not to be construed as being limiting in any way.

EXAMPLE 1

(a) Single Crystal Lanthanum Fluoride Solid Electrolyte Fuel Cell $LaF_3$ single crystals (purity 99.99 percent; diameter; 10 mm) were purchased from Optovac, Incorporated, North Brookfield, Mass. 01535, and were sliced into disks 25 mil (0.64 mm) thick. The nominal ionic conductivity of the $LaF_3$ single crystals is about $10^{-7}$ S/cm at room temperature. Platinum black that is made by a thermal decomposition of a Pt salt is used as an electrocatalyst for both oxygen cathode and hydrogen anode. A typical catalyst loading is about 25–30 mg/cm². The procedure for depositing Pt black catalyst onto the $LaF_3$ single-crystal disk is as follows:

(1) Place a tiny 0.002–0.005 mL) of a concentrated (about 2 M) $H_2PtCl_6$ aqueous solution on one side of a $LaF_3$ disk (previously cleaned with methanol), and using a metal rod, spread the solution into a circular spot with a diameter of about 4 or 5 mm.

(2) Place the above sample into an electric furnace. Increase the temperature of the furnace very slowly at a rate of about 4° C./min so as not to break the $LaF_3$ disk by a thermal shock, and maintain the temperature of the furnace at 200° C. for about 20 min for the thermal decomposition of the Pt salt in a gentle mixed-gas stream (flow rate: 30–50 mL/min) consisting of 10 percent $H_2$ and 90 percent $N_2$.

(3) Cool the furnace extremely slowly at a rate of 2° C./min. Then carefully remove the sample from the furnace.

(4) Repeat the above procedure several times until a desired catalyst loading is obtained; then, repeat the entire procedure for the other side of the $LaF_3$ disk.

(b) Test for Formation of HF or $F_2$

The exhausted gas from the anodic compartment of the $H_2/O_2$ fuel-cell of Part (a) based on a single crystal $LaF_3$ pellet under a short-circuit operating condition is introduced into a beaker containing 30 mL of a 5 percent $CaCl_2$ aqueous solution (about $1.4 \times 10^{-2}$ mol/30 mL or about 0.45 M). If HF, $F_2$, or both are produced at the anode, white colloids of $CaF_2$ precipitates will be formed according to the following reaction:

$$CaCl_2 + 2F^- \text{(or } F_2\text{)} \rightarrow CaF_2(s.) + 2Cl^- \text{ (or } Cl_2\text{)} \quad (9)$$

Reaction (9) has a solubility constant $K_{sp}$ of $1.6 \times 10^{-10}$ for $CaF_2$ ($Ksp(CaF_2) = [Ca^{2+}][F^-]^2$). Therefore, 30 mL of 5 percent $CaCl_2$ aqueous solution is sensitive enough to detect the presence of $F^-$ ions in a concentration greater than $1.8 \times 10^5$ M or $5.5 \times 10^{-7}$ moles. The test was continued for 120 hours with an average $I_{sc}$ of 20 μA, which corresponds to 8.6 Coulombs, and $9 \times 10^{-5}$ mols of $F^-$ ions should be produced if HF (or $F_2$) is produced at 100 percent efficiency. The solution remained clear after this prolonged test, indicating no evidence for the formation of HF or $F_2$.

EXAMPLE 2

Preparation of Polycrystalline $La_{0.94}Sr_{0.06}F_{2.94}$ 50 g of $LaCl_3 \cdot H_2O$ (Reacton-M; 99.99 percent, Alpha Products, Danvers, Mass.; Stock 500062) and 2.38 g of $SrCl_2 \cdot 6H_2O$ (Puratronic; 99.9965 percent Alpha Products, Danvers, Mass.; Stock 400267) are dissolved in 500 mL of deionized water with 1 mL of concentrated reagent-grade HCl on a magnetic stirrer until free of solids. A solution of 80 mL of buffered oxide etch (prepared by KTI Chemicals of Sunnyvale, Calif., by mixing 8.01 g of 42 percent $NH_4F$ with 1.31 g of 49 percent HF) in 400 mL deionized water is added as rapidly as possible with brisk stirring to encourage the maximum degree of coprecipitation. After about two minutes of vigorous stirring, the suspension is allowed to settle and a few drops of buffered oxide etch are added to check for complete precipitation. The material is washed three times by decantation and settling. Further washing results in peptization (i.e. formation of a colloidal suspension in the ion-free water), as indicated by a haze in the supernatant liquid.

The mixture is filtered through Whatman No. 1 filter paper with limited washing with deionized water to aid in the transfer. The solids and paper were dried overnight to 120° C. or until visibly dry. The solid is removed from the filter paper and transferred to a quartz boat and calcined in argon in a tube furnace at 950° C. overnight so as to drive off the residual $H_2O$, $NH_4Cl$, and $NH_4F$. The calcined material is ground to pass a 100-mesh screen. The particles are then all much less than 0.01 inch (250 $\mu$m) in diameter. The pressed and sintered pellets are prepared by hot pressing in a heated graphite die at 1100° C. and 15,000 pounds for 15 minutes. The resultant 0.5 inch-diameter rod is sliced to 1-mm thick disks.

EXAMPLE 3

DEPTH PROFILE BY AUGER ELECTRON SPECTROSCOPY

Auger electron spectroscopy (AES) analysis was employed to obtain the depth profile of the polycrystalline $LaF_3$ pellet that was used in a long-term fuel-cell test. In high-energy Auger spectra, characteristic peaks are obtained for the elements of our concern, viz. oxygen, lanthanum, and fluorine at 503, 625, and 647 eV, respectively. FIGS. 17 A, B and C show the Auger depth profile of the used sample as well as of a virgin $LaF_3$ pellet for comparison. Unfortunately, it is not known which end is anode or cathode. The y axis corresponds to the concentrations of these elements on arbitrary scale. No substantial difference was observed in the depth profile of lanthanum. A major redistribution of elemental fluorine is seen in the used sample; however, no substantial net decease of fluorine concentration is noted. A most encouraging finding is an apparent dramatic increase in the oxygen concentration in the used sample. The AES results strongly indicate that oxide ion ($O^{2-}$) are, indeed, generated at the cathode by the $H_2/O_2$ fuel-cell operation and transported to the anode, where they are consumed by a reaction with hydrogen with little production of such side products as HF and $F_2$.

EXAMPLE 4

STAINLESS STEEL POROUS SUBSTRATES

Porous stainless-steel materials are most preferred as the substrates on which thin films of $La_{1-x}Sr_xF_{3-x}$ can be deposited for the following reasons:

Thermal coefficient of expansion of stainless steel (#316: $16 \times 10^{-6}$/°C.; #304: $17.3 \times 10^{-6}$/°C.) is close to that of $LaF_3$ materials (about $17.2 \times 10^{-6}$/°C.).

Stainless steel is relatively inert.

A porous stainless steel serves not only as a substrate but also as a current collector.

Porous stainless steel substrates are purchased from Pall Porous Metals Filter Corporation (PALL), East Hills, N.Y. 11548, and from Sintered Specialties, Incorporated (SSI), Janesville, Wis. 53547. Table 4 summarizes their physical properties. These porous stainless steel materials are originally designed as filters for fluid clarification in high temperature, high pressure, and corrosive environments.

TABLE 4

| Physical Properties of Stainless-Steel Substrates | | | |
|---|---|---|---|
| Manufacturer | Catalog Number | Pore Size ($\mu$m) | Porosity (%) |
| PALL | PO5 | 0.5 | 42 |
| PALL | PO9 | 2.0 | 36 |
| SSI | S-2930 | 2.0 | 10 |
| SSI | S-2929 | 3.0 | 14 |

The Pall materials are rougher and have higher porosity; thus, they are attractive for our fuel-cell application because they potentially can provide a large number of triple-interface reaction sites. However, the deposition of $LaF_3$ films on the PALL materials is not easy because of their wide open structures. Indeed, the PALL PO9 (nominal pore size 2 $\mu$m) was found to be too coarse to use. So far, the PALL material with nominal pore size of 0.5 $\mu$m (see FIG. 18A) has been identified as the best substrate for experiments. One difficulty associated with this material is, however, that although the manufacturer states (nominal) pore size to be 0.5 $\mu$m, the actual size of individual pores varies from 0.2 $\mu$m to as high as 40 $\mu$m, which makes the deposition of $LaF_3$ films difficult. The SSI materials are substantially flatter and have pores much closer to the state 2 and 3 $\mu$m, with a concomitant lowering in the porosity. The deposition of $LaF_3$ films should be easier with the SSI materials; however, their porosity is too low to provide enough triple interface reaction sites.

EXAMPLE 5

Preparation Method of Platinum-Based Hydrogen Oxidation Electrocatalyst on a Porous Stainless Steel Substrate The deposition of a hydrogen electrocatalyst is one of the key steps for the successful fabrication of the thin-film $La_{1-x}B_xF_{3-x}$ solid electrolyte fuel-cell. The electrocatalyst is deposited on the porous stainless-steel substrate in such a way that the resulted coating provides not only an ideal triple-interface but also a "smooth" surface necessary for the deposition of $LaF_3$ layer. In the first set of experiments, PALL PO5 (0.5 $\mu$m nominal pore size) as the substrate and platinum as the hydrogen oxidation electrode material are examined:

Method 1

Thermal Decomposition of a Platinum Salt (a) Drop concentrated hydrous hexaplatinic acid solution (1 M) on a substrate.

(b) Dry it in a furnace at 450° C. for about 1 hr in $H_2$/Ar mixture gas.

Method 2

Physical Deposition of Platinum Black Power Powder followed by Thermal Decomposition of a Platinum Salt (a) Mix platinum black powder into xylene (some of the platinum black dissolves into the solvent while most of the platinum black remains as powder at the bottom of the container).

(b) Put stainless steel into the solution and pick up the bottom solution by a squeezer so that this solution contains much Pt black powder.

(c) Put this solution on top of the stainless steel under the agitation of an ultrasonic bath. Platinum powder will spread out on the whole surface of porous stainless steel which partly encloses the cavities.

(d) Pick up the substrate and dry it until the xylene evaporates.

(e) Drop $H_2PtCl_6$ solution on the substrate and dry it in a furnace as described in Method 1.

Method 3

Electrochemical Deposition of Platinum In An Alkaline Solution (a) Make up the solution of the following composition:

| | |
|---|---|
| platinum as $H_2PtCl_6$ | 10 g/L |
| ammonium phosphate | 60 g/L |
| ammonium hydroxide to pH | 7.5–9 |

(b) Deposit platinum by applying a constant potential of −550 to about −700 mV versus SCE at about 70° C. under the stirring condition for 20–30 minutes to several hours, depending upon a desired catalyst loading.

Method 1 produces a very rough surface with cracked $PtO_x$ layers, which is not favorable for the $LaF_3$ deposition. It is thought that the application of platinum black powder onto the substrate would result in the pores that are partly filled with the platinum black, and the successive Pt deposition by the thermal decomposition method would completely fill the pores with Pt (Method 2). The resultant surface is much smoother than the one made by Method 1, however, there are still some unfilled, big cavities, and the deposited Pt is very flaky. Therefore, the surface made by Method 2 is not ideal either for the deposition of $LaF_3$.

Because the first two methods did not turn out to be effective for our purpose, an electroplating method (Method 3), i.e. a constant potential method, was introduced for the deposition of Pt catalyst layers. FIG. 18B shows the surface morphology of the platinum layers formed at about −670 mV versus SCE for 2.5 hours. The surface morphology of the electroplated platinum depends strongly upon the applied potential; a platinum "black" film is obtained when the applied potential is in the range of about −600 mV to about −700 mV versus SCE, while the potential of about −500 mV to about −600 mV versus SCE produces a more metallic-looking Pt film. The cut-off potential appears to be related to the competing hydrogen evolution reaction which initiates around −600 mV. In the case of metallic Pt, the pores appear to be totally clogged with Pt and few gas molecules can go through. Therefore, PALL P05 porous stainless steel (0.5 μm nominal pore size) substrates that are electrochemically plated with Pt catalyst layer at about −670 mV for 2.5 hours are found to be the most desirable for the $LaF_3$ depositions. The estimated Pt catalyst loading is in the range of 20–30 mg/cm². The surface consists of small clusters of platinum and exhibits more compact, "smooth" morphology, compared to the surfaces made by other Methods 1 and 2.

EXAMPLE 6

Preparation of Perovskite Powder $La_{1-x}Sr_xCoO_3$ by Freeze-Drying Method (a) Four aqueous solutions of $La_{1-x}Sr_xCoO_3$ with x=0.1, 0.2, 0.4 and 0.94 are made using acetates of lanthanum, strontium and cobalt. Each solution is diluted using distilled water to 0.13 molality in cobalt.

(b) The solutions are then ultrasonically sprayed into stainless steel pans containing liquid nitrogen. The pans of frozen droplets were then placed into the freeze-dryer.

(c) After the liquid nitrogen evaporates, the vacuum is switched on and the dryer program is engaged.

(d) After the droplets are dried for 3 days, they are removed from the dryer and placed in $Al_2O_3$ crucibles for calcining.

(e) Calcining is done at 600° C. for 10 hours and then at 800° C. for 4 hours in flowing oxygen.

(f) Samples are removed from crucibles and placed directly into vials without any attempts to break up any agglomerates formed.

The perovskite powder is first mixed with a binder material-water glass (about 10 weight percent) made of sodium meta silicate. The slurry is coated onto the lanthanum fluoride film followed by a sintering treatment in air of 450° C. to 500° C. for 1 hour. The perovskite forms a physical combination with the electrolyte on the support. The above procedure is also used to make perovskite with minor changes. Cobalt acetate is replaced by nickel and manganese acetates.

EXAMPLE 7

Deposition of Thin-Films of $La_{1-x}Sr_xF_{3-x}$ on Porous Substrates by Thermal Evaporation FIGS. 19 and 20 illustrate the vacuum deposition station 19 used to deposit a thin film of $La_{1-x}Sr_xF_{3-x}$ on a porous stainless steel substrate ("sample"). The samples are placed into the sample holder 51, which holds up to four samples. The vacuum system is prepared for the deposition by replacing the thickness monitor crystal 58 and by filling the evaporation boats 53 with source material 54. The thickness monitor 58 calculates the thickness by measuring the amount of material evaporated onto the crystal and calculates the thickness from the density. If microcracks occur on the crystal, it ceases to function; and having a finite lifetime, it must be changed before each series of depositions. The tantalum evaporation boats 53 are filled with source material 54. The source material is either optical grade 99.999% crystalline $LaF_3$, 99.999% crystalline $SrF_2$, or a mixture of 99.999% $LaF_3$ powder and 99.994% $SrF_2$. Two evaporation source boats 53 are used to maximize the amount of material that can be deposited during one pump-down cycle of the vacuum chamber 55. The samples are placed in the chamber with the surface for the deposition perpendicular to the gas stream from the evaporation. In what follows, a typical deposition procedure is given:

(a) The chamber 55 is first flooded with $N_2$ for several minutes to remove $O_2$ and water vapor from the chamber.

(b) The pump 56 (turbo) and backing pump 57 are switched on and the chamber 55 is pumped down to $10^{-7}$ torr. Before deposition, the source material needs to be outgassed for approximately 1 hour with a current of 40 amps through the boat.

(c) Turn on Inficon Xtal monitor that measures deposition rate and start water flow to cool the monitor crystal. Normally, the substrate temperature is around 175° C. without water cooling. Increase the current through the boat to approximately 75A until the monitor reads the desired deposition rate, i.e. 3–5Å/s, which depends on resistances due to the boat geometry, source material, and pressure. At this rate, deposition of about 10 μm film takes approximately 5 hours.

(d) Open shutter to expose substrates to gas stream and monitor the deposition parameters, i.e. time, rate, thickness, and pressure. Adjust current to keep constant deposition parameters, as needed.

(e) Repeat outgas and deposition (i.e. steps a through d) with second boat, if a thicker film is desired.

(f) Allow samples to cool. Remove and characterize.

Additional features of FIGS. 19 and 20 include the apparatus support 59. The thickness monitor crystal 58, which is connected to wire 60 which exits vacuum chamber 61 and is referred to as the thickness monitor outlet. The tube support 62, shutter 63 and shield 64 are seen in both FIGS. 19 and 20.

FIG. 21 shows a typical example of the deposited $LaF_3$ films with or without platinum catalyst layer. A $LaF_3$ film was directly deposited on an SSI S-2930 porous stainless steel substrate. It can be seen that crystallites of $LaF_3$ grow almost perpendicular to the substrate plane, i.e. the direction to the evaporation source. The deposited $LaF_3$ film, unfortunately, exactly reflects the surface "roughness" of the substrate; viz. the film consists of many small islands surrounded with cracks, which may lower the energy density of the fuel cell through the possible cross-talk of gases.

While some embodiments of the invention have been shown and described herein, it will become apparent to those skilled in the art that various modifications and changes can be made in the present invention regarding solid materials for use as electrodes solid electrolytes in fuel cell applications, without departing from its spirit and scope. All such modifications and changes coming within the scope of the appended claims are intended to be covered thereby.

We claim:

1. The use of a solid $O^{2-}$ (oxide ion) conducting material as an electrolyte for a fuel-cell, said material comprising:

a monocrystal or polycrystal structure of the formula $$A_{1-x}B_xZ \quad (AA)$$

wherein
A is independently selected from lanthanum, cerium, neodymium, scandium or mixtures thereof;
B is independently selected from strontium, calcium, barium or magnesium, and
x is between 0 and 0.9999,
Z is selected from the group consisting of $F_{3-x}$ and $O_cF_d$ where F is fluorine, O is oxygen, x is between about 0 and 0.9999 and $2c+d=3-x$,
wherein c is between 0.0001 and 1.5 and d is between 0.001 and less than or equal to 3, wherein the solid material as an electrolyte is a thin layer having one side in contact with an electrode which is in contact with a gaseous fuel for a fuel cell and the other side of the thin solid material for the electrolyte is also in contact with an electrode which is in contact with gaseous oxygen, or air or mixtures thereof.

2. The use of the solid material of claim 1 wherein A is lanthanum.

3. The use of the solid material of claim 2 wherein B is strontium.

4. The use of the solid material of claim 3 wherein Z is $F_{3-x}$.

5. The use of the solid material of claim 3 wherein Z is $O_cF_d$ and wherein the oxygen is an integral part of the crystal lattice.

6. The use of the solid material of claim 4 wherein A is lanthanum, Z is $F_{3-x}$, and x is 0, and the solid material is a polycrystal.

7. The use of the solid material of claim 1 wherein the solid material as a polycrystal has a thickness between about 1 and 300 micrometers.

8. The use of the solid material of claim 7 wherein solid material as a polycrystal has a thickness between about 1 and 300 micrometers.

9. The use of the solid material of claim 1 as a fuel cell to generate an electrical current at a temperature of between about 20° and 300° C.

10. The use of the solid material of claim 8 as a fuel cell to generate an electrical current at a temperature of between about 20° and 300° C.

11. The use of a solid electrolyte fuel cell comprising a structure:

$$C—E—A'—S$$

wherein
a first electrode material (C), which is only in contact with
a thin film solid electrolyte (E) which is also separately in contact with
a second electrode material A' which is also separately in contact with a porous mechanical support material (S),
wherein the thin film solid electrolyte (E) has the structure:

$$A_{1-x}B_xZ$$

wherein
A is independently selected from lanthanum, cerium, neodymium, scandium or mixtures thereof;
B is independently selected from strontium, calcium, barium or magnesium,
x is between 0 and 0.9999,
Z is selected from the group consisting of $F_{3-x}$ and $O_cF_d$ where F is fluorine, O is oxygen, x is between about 0 and 0.9999 and $2c+d=3-x$,
wherein c is between 0.0001 and 1.5 and d is between 0.001 and less than or equal to 3, wherein the solid material as an electrolyte is a thin layer having one side in contact with an electrode which is in contact with a gaseous fuel for a fuel cell and the other side of the thin solid material for the electrolyte is also in contact with an electrode which is in contact with gaseous oxygen, or air or mixtures thereof.

12. The use of the solid electrolyte fuel cell of claim 11 wherein the first electrode material is in contact with an oxidizing gas and the second electrode material is in contact with a reducing gas.

13. The use of the solid electrolyte fuel cell of claim 11 wherein the first electrode material is in contact with a reducing gas and the second electrode material is in contact with an oxidizing gas.

14. The use of the solid electrolyte fuel cell of claim 11 wherein the porous support is colloidal alumina.

15. The use of the solid electrolyte fuel cell of claim 11 wherein the thin film solid electrolyte has a thickness of between about 1 and 300 microns.

16. The use of the solid electrolyte fuel cell of claim 15 wherein in the thin film solid electrolyte B is strontium.

17. The use of the solid electrolyte fuel cell of claim 16 wherein the thin film solid electrolyte A is lanthanum.

18. The use of the solid electrolyte fuel cell of claim 17 wherein x is between about 0.0001 and 0.2.

19. The use of the solid electrolyte fuel cell of claim 19 wherein x is about 0.1.

20. The use of the solid electrolyte fuel cell of claim 19 wherein the thin film has a thickness of about 10 micrometers.

21. The use of the solid material of claim 1 an electrolyte for a fuel cell at a temperature of between about 200° and 500° C.

22. The use of the solid electrolyte fuel cell of claim 11 at a temperature of between about 300° to 500° C.

23. The use of the solid electrolyte fuel cell of claim 11 wherein the second electrolyte material is in contact with a porous metallic mechanical support which also functions as a current collector.

24. The use of the solid electrolyte fuel cell of claim 23 wherein the porous metallic support is selected from stainless steel or nickel.

25. The use of a solid electrolyte fuel cell comprising a structure:

C—E—A'—S wherein
a first electrode material (C), which is only in contact with
a thin film solid electrolyte (E) which is also separately in contact with
a second electrode material (A') which is also separately in contact with a porous mechanical support material (S),
wherein the thin film solid electrolyte (E) has the structure:

$A_{1-x}B_xZ$ wherein
A is independently selected from lanthanum, cerium, neodymium, scandium or mixtures thereof;
B is independently selected from strontium, calcium, barium, or magnesium,
x is between 0 and 0.9999,
Z is selected from the group consisting of $F_{3-x}$ and $O_cF_d$ where F is fluorine, O is oxygen, x is between about 0 and 0.9999 and $2c+d=3-x$,
where c is between 0.0001 and 1.5 and d is between 0.001 and less than or equal to 3,
wherein either the first electrode material (C) or second electrode material (A') comprises $A_{1-x}B_xQO_3$ having a perovskite or perovskite-type structure as an electrode catalyst in combination with $A_{1-x}B_xZ$ as a polycrystalline solid electrolyte wherein
A is independently selected from lanthanum, cerium, neodymium, praseodymium or scandium,
B is independently selected from strontium, calcium, barium or magnesium,
Q is independently selected from nickel, cobalt, iron or manganese and x is between about 0 and 0.9999,
Z is selected from the group consisting of $F_{3-x}$ and $O_cF_d$ where F is fluorine, O is oxygen, x is between about 0 and 0.9999 and $2c+d=3-x$, and
c is between 0.0001 and 1.5 and d is between 0.0001 and less than or equal to 3.

26. The solid electrolyte fuel cell of claim 25 wherein A is lanthanum, B is strontium, Q is cobalt, Z is $F_{3-x}$ and x is greater than 0 and less than 0.5.

27. A solid electrolyte fuel cell comprising a structure:

C—E—A'—S wherein
a first electrode material (C), which is only in contact with
a thin film solid electrolyte (E) which is also separately in contact with
a second electrode material (A') which is also separately in contact with a porous mechanical support material (S),
wherein the thin film solid electrolyte (E) has the structure:

$A_{1-x}B_xZ$ wherein
A is independently selected from lanthanum, cerium, neodymium, scandium or mixtures thereof;
B is independently selected from strontium, calcium, barium, or magnesium,
x is between 0 and 0.9999,
Z is selected from the group consisting of $F_{3-x}$ and $O_cF_d$ where F is fluorine, O is oxygen, x is between about 0 and 0.9999 and $2c+d=3-x$,
where c is between 0.0001 and 1.5 and d is between 0.001 and less than or equal to 3, with the proviso when A is lanthanum, Z is $F_{3-x}$ and x is 0, the solid material is only a monocrystal,
wherein the cathode material is $A_{1-x}B_xQO_3$;
wherein O is oxygen, A is independently selected from lanthanum, cerium, neodymium, praseodymium, scandium or mixtures thereof;

B is independently selected from calcium, barium or magnesium;

Q is selected manganese, iron, cobalt or nickel, and x is between about 0 and 0.8.

28. The use of the solid electrolyte fuel cell of claim 11 wherein A in the porous mechanical support material (S) is selected from electrically conducting metallic material or non-electrically conducting material.

29. The use of the solid electrolyte of claim 28 wherein S has a pore size of between about 0.05–5 μm, a porosity between about 40–80% and a thickness of between about 200 micrometers and 5 millimeters.

30. The use of a solid material as an electrolyte for a fuel cell, said material comprising:

a monocrystal or polycrystal structure of the formula:

wherein $Pb_eSn_fF_g$

Pb is lead,

Sn is tin, with the proviso that when f is 1, e is 1 and g is 4, and when f is 0, e is 1, and g is 2, wherein the solid material is an electrolyte is a thin layer having one side in contact with an electrode which is in contact with a gaseous fuel for a fuel cell and the other side of the thin solid material for the electrolyte is also in contact with an electrode which is in contact with gaseous oxygen, or air or mixtures thereof.

31. The solid material of claim 30 wherein $Pb_eSn_fF_g$ is $PbSn_{74}$.

32. The solid material of claim 30 wherein $Pb_eSn_fF_g$ is $PbF_2$.

* * * * *